US009006411B2

(12) United States Patent
Kobayashi

(10) Patent No.: US 9,006,411 B2
(45) Date of Patent: Apr. 14, 2015

(54) NEURON-SPECIFIC RETROGRADE TRANSPORT VECTOR

(75) Inventor: Kazuto Kobayashi, Fukushima (JP)

(73) Assignee: Japan Science and Technology Agency, Kawaguchi-Shi, Saitama (JP)

( * ) Notice: Subject to any disclaimer, the term of this patent is extended or adjusted under 35 U.S.C. 154(b) by 0 days.

(21) Appl. No.: 13/988,973

(22) PCT Filed: Nov. 25, 2011

(86) PCT No.: PCT/JP2011/077142
§ 371 (c)(1),
(2), (4) Date: Jul. 23, 2013

(87) PCT Pub. No.: WO2012/070639
PCT Pub. Date: May 31, 2012

(65) Prior Publication Data

US 2013/0315872 A1 Nov. 28, 2013

(30) Foreign Application Priority Data

Nov. 26, 2010 (JP) ................................ 2010-263148

(51) Int. Cl.

*C07K 14/005* (2006.01)
*A01N 63/00* (2006.01)
*A01N 65/00* (2009.01)
*C12N 15/86* (2006.01)
*A61K 48/00* (2006.01)

(52) U.S. Cl.

CPC ........ *C12N 15/86* (2013.01); *C12N 2810/6081* (2013.01); *A61K 48/0058* (2013.01); *C07K 14/005* (2013.01); *C07K 2319/00* (2013.01); *C07K 2319/03* (2013.01); *C12N 2740/16045* (2013.01); *C12N 2740/16071* (2013.01); *C12N 2760/20122* (2013.01); *C12N 2760/20222* (2013.01)

(58) Field of Classification Search

None
See application file for complete search history.

(56) References Cited

U.S. PATENT DOCUMENTS

2003/0124146 A1 7/2003 Schnell et al.
2004/0071675 A1 4/2004 Mazarakis et al.

FOREIGN PATENT DOCUMENTS

EP 2 508 599 A1 10/2012
JP 2009-034029 2/2009

OTHER PUBLICATIONS

Kato, et al. (ePub Sep. 9, 2011) "Neuron-Specific Gene Transfer Through Retrograde Transport of Lentiviral Vector Pseudotyped with a Novel Type of Fusion Envelope Glycoprotein", Human Gene Therapy, 22(12): 1511-23.*

Luke Timmerman, http://www.xconomy.com/boston/2009/03/31/genzyme-gene-therapy-fails-to-help-people-with-leg-disease-walk-longer/ (2009) Published by Xconomy online, Boston, Mass., no author, no volume, no number, no journal, no pages, 5 pages long printed.*

Palfi, et al. (Mar. 29, 2014) "Long-term safety and tolerability of ProSavin, a lentiviral vector-based gene therapy for Parkinson's disease: a dose escalation, open label, phase ½ trial", The Lancet, 383: 1138-46.*

Coune, et al. (2012) "Parkinson's Disease: Gene Therapies", Cold Spring Harbor Perspectives in Medicine, 2:a009431, pp. 1-15.*

Kitagawa, R. et al. "Differential characteristics of HIV-based versus SIV-based lentiviral vector systems: Gene delivery to neurons and axonal transport of expressed gene", Neuroscience Research, vol. 57, Issue 4, Apr. 2007, pp. 550-558.

Desmaris, N. et al., "Production and Neurotropism of Lentivirus Vectors Pseudotyped with *Lyssavirus* Envelope Glycoproteins", Molecular Therapy, 2001, vol. 4, pp. 149-156.

Mazarakis, N. D. et al., "Rabies virus glycoprotein pseudotyping of lentiviral vectors enables retrograde axonal transport and access to the nervous system after peripheral delivery", Human Molecular Genetics, 2001,vol. 10, Issue 19, pp. 2109-2121.

Kato, S. et al., "Efficient Gene Transfer via Retrograde Transport in Rodent and Primate Brains Using a Human Immunodeficiency Virus Type 1-Based Vector Pseudotyped with Rabies Virus Glycoprotein", Human Gene Therapy, Nov. 2007, vol. 18, No. 11, pp. 1141-1152 (Abstract only).

Kato, S. et al., "Neuron-Specific Gene Transfer Through Retrograde Transport of Lentiviral Vector Pseudotyped with a Novel Type of Fusion Envelope Glycoprotein", Human Gene Therapy, Dec. 2011, vol. 22(12), pp. 1511-1523 (Abstract only).

Kato, S. et al., "A Lentiviral Strategy for Highly Efficient Retrograde Gene Transfer by Pseudotyping with Fusion Envelope Glycoprotein", Human Gene Therapy, Feb. 2011, vol. 22(2), pp. 197-206.

(Continued)

*Primary Examiner* — Robert M Kelly
(74) *Attorney, Agent, or Firm* — Ping Wang; Andrews Kurth LLP

(57) ABSTRACT

The present invention provides a lentiviral vector system having a higher titer, while sustaining an excellent retrograde transport ability, particularly, in the brain.

The present invention also provides a kit for preparing a retrograde transport viral vector comprising:

(1) a packaging plasmid containing the gag gene and the pol gene of HIV-1;
(2) a packaging plasmid containing an accessory gene of HIV-1;
(3) a transfer plasmid containing an target gene (a transgene); and
(4) an envelope plasmid containing, as an envelope gene, a gene encoding a fused polypeptide comprising a fused extracellular domain consisting of the N-terminal region of an extracellular domain of rabies virus glycoprotein (RV-G) and the C-terminal region of an extracellular domain of vesicular stomatitis virus glycoprotein (VSV-G), a transmembrane domain of RV-G or VSV-G, and an intracellular domain of VSV-G, and the like.

3 Claims, 7 Drawing Sheets

(56) References Cited

OTHER PUBLICATIONS

Foley, H. D. et al., "A recombinent rabies virus expressing vesicular stomatitis virus glycoprotein fails to protect against rabies virus infection," PNAS, Dec. 19,2000, pp. 14680-14685, vol. 97, No. 26.
Morimoto, K. et al., "High level of expression of a human rabies virus-neutralizing monoclonal antibody by a rhabdovirus-based vector," Journal of Immunological Methods, 2001, pp. 199-206, vol. 252.
Mochizuki, H. et al., "High-Titer Human Immunodeficiency Virus Type 1-Based Vector Systems for Gene Delivery into Nondividing Cells," Journal of Virology, Nov. 1998, pp. 8873-8883, vol. 72, No. 11.
Kordower, J. H. et al., "Neurodegeneration Prevented by Lentriviral Vector Delivery of GDNF in Primate Models of Parkinson's Disease," Science, Oct. 2000, pp. 767-773, vol. 290.
Marr, R. A., et al., "Neprilysin Gene Transfer Reduces Human Amyloid Pathology in Transgenic Mice," The Journal of Neuroscience, Mar. 15, 2003, pp. 1992-1996, vol. 23, No. 6.
Lo Bianco, C. et al., "Lentiviral vector delivery of parkin prevents dopaminergic degeneration in an α-synuclein rat model of Parkinson's disease," PNAS, Dec. 14, 2004, pp. 17510-17515, vol. 101, No. 50.
Naldini, L. et al., "Efficient transfer, integration, and sustained long-term expression of the transgene in adult rat brains injected with a lentiviral vector," Proc. Natl. Acad. Sci., Oct. 1996, pp. 11382-11388, vol. 93.
Reiser, J. et al., "Transduction of nondividing cells using pseudotyped defective high-titer HIV type 1 particles," Proc. Natl. Acad. Sci., Dec. 1996, pp. 15266-15271, vol. 93.
Mitrophanous, K. A. et al., "Stable gene transfer to the nervous system using a non-primate lentiviral vector," Gene Therapy, 1999, pp. 1808-1818, vol. 6.
Azzouz, M. et al., "VEGF delivery with retrogradely transported lentivector prolongs survival in a mouse ALS model," Nature, May 27, 2004, pp. 413-417, vol. 429.
Supplementary European Search Report of Application No. 10834471 mailed May 29, 2013.
Kato, S. et al., "Efficient Gene Transfer via Retrograde Transport in Rodent and Primate Brains Using a Human Immunodeficiency Virus Type 1-Based Vector Pseudotyped with Rabies Virus Glycoprotein", Human Gene Theraphy, Nov. 2007, vol. 18, Issue 11, pp. 1141-1152 (Abstract only).
Kato, S. et al., "Neuron-Specific Gene Transfer Through Retrograde Transport of Lentiviral Vector Pseudotyped with a Novel Type of Fusion Envelope Glycoprotein", Human Gene Theraphy, Dec. 2011, vol. 22, Issue 12, pp. 1511-1523 (Abstract only).
Kuramochi, M. et al., "Highly efficient retrograde gene transfer system by a lentiviral vector pseudotyped with fusion envelope glycoprotein for the study of structure and function of neural circuit", Society for Neuroscience, 2010 (Abstract only).
Inoue, K. et al., "Efficient retrograde gene transfer into primate brain with an HIV-1 based lentiviral vector pseudotyped with rabies virus glycoprotein", Society for Neuroscience, 2008 (Abstract only).
Supplementary European Search Report of Application No. 11843579.1 mailed Apr. 15, 2014.
Carpentier, D. C. J., et al., "Enhanced pseudotyping efficiency of HIV-1 lentiviral vectors by a rabies/vesicular stomatitis virus chimeric envelope glycoprotein", Gene Ther., Jul. 2012, vol. 19(7), pp. 761-774.
Schaffer, D. V., et al., "Molecular engineering of viral gene delivery vehicles", Annual Review of Biomedical Engineering, 2008,vol. 10, pp. 169-194.

* cited by examiner

Fig.7

ATGGTTCCGCAGGTTCTTTTGTTTGTACTCCTTCTGGGTTTTTCGTTGTGTTTCGG
GAAGTTCCCCATTTACACGATACCAGACGAACTTGGTCCCTGGAGCCCTATTGACA
TACACCATCTCAGCTGTCCAAATAACCTGGTTGTGGAGGATGAAGGATGTACCAA
CCTGTCCGAGTTCTCCTACATGGAACTCAAAGTGGGATACATCTCAGCCATCAAA
GTGAACGGGTTCACTTGCACAGGTGTTGTGACAGAGGCAGAGACCTACACCAACT
TTGTTGGTTATGTCACAACCACATTTAAGAGAAAGCATTTCCGCCCCACCCCAGAC
GCATGTAGAGCCGCGTATAACTGGAAGATGGCCGGTGACCCCAGATATGAAGAGT
CCCTACACAATCCATACCCCGACTACCACTGGCTTCGAACTGTAAGAACCACCAAA
GAGTCCCTCATTATCATATCCCCAAGTGTGACAGATTTGGACCCATATGACAAATC
CCTTCACTCAAGGGTCTTCCCTGGCGGAAAGTGCTCAGGAATAACGGTGTCCTCT
ACCTACTGCTCAACTAACCATGATTACACCATTTGGATGCCCGAGAATCCGAGACC
AAGGACACCTTGTGACATTTTTACCAATAGCAGAGGGAAGAGAGCATCCAACGGG
AACAAGACTTGCGGCTTTGTGGATGAAAGAGGCCTGTATAAGTCTCTAAAAGGAG
CATGCAGGCTCAAGTTATGTGGAGTTCTTGGACTTAGACTTATGGATGGAACATG
GGTCGCGATGCAAACATCAGATGAGACCAAATGGTGCCCTCCAGATCAGTTGGTG
AATTTGCACGACTTTCGCTCAGACGAGATCGAGCATCTCGTTGTGGAGGAGTTAG
TCAAGAAAAGAGAGGAATGTCTGGATGCATTAGAGTCCATCATGACCACCAAGTC
AGTAAGTTTCAGACGTCTCAGTCACCTGAGAAAACTTGTCCCAGGGTTTGGAAAA
GCATATACCATATTCAACAAAACCTTGATGGAGGCTGATGCTCACTACAAGTCAGT
CCGGACCTGGAATGAGATCATCCCCTCAAAAGGGTGTTTGAAAGTTGGAGGAAGG
TGCCATCCTCATGTGAACGGGGTGTTTTTCAATGGTATAATATTAGGGCCTGACGA
CCATGTCCTAATCCCAGAGATGCAATCATCCCTCCTCCAGCAACATATGGAGTTGT
TGGAATCTTCAGTTATCCCCCTGATGCACCCCCTGGCAGACCCTTCTACAGTTTTC
AAAGAAGGTGATGAGGCTGAGGATTTTGTTGAAGTTCACCTCTCCAAAAATCCA
ATCGAGCTTGTAGAAGGTTGGTTCAGTAGTTGGAAAAGCTCTATTGCCTCTTT
TTTCTTTATCATAGGGTTAATCATTGGACTATTCTTGGTTCTCCGAGTTGCTAT
CCATCTTTGCATTAAATTAAAGCACACCAAGAAAAGACAGATTTATACAGACAT
AGAGATGAACCGACTTGGAAAGTAA SEQ ID NO:1

Bold type : N terminal region of RV-G extracellular domain
Framed type : C terminal region of VSV-G extracellular domain
Underlined type : Transmembrane domain of VSV-G
Double-underlined type : Intracellular domain of VSV-G

NEURON-SPECIFIC RETROGRADE TRANSPORT VECTOR

This application is a National Stage Application of PCT/JP2011/077142, filed Nov. 25, 2011, which claims priority from Japanese Patent Application No. 2010-263148, filed Nov. 26, 2010. The entirety of all of the aforementioned applications is incorporated herein by reference.

FIELD

The present invention relates to a neuron-specific retrograde transport vector (NeuRet) system, having an excellent retrograde transport ability; particularly, in the brain. The vector system has high production efficiency, particular enabling a selective transfer or introduction of a gene into the neuron. More specifically, the present application relates to a lentiviral vector system which is pseudotyped by a fused polypeptide comprising a fused extracellular domain consisting of the N-terminal region of an extracellular domain of rabies virus glycoprotein (RV-G) and the C-terminal region of an extracellular domain of vesicular stomatitis virus glycoprotein (VSV-G), a transmembrane domain of RV-G or VSV-G and an intracellular domain of VSV-G; and a method of gene transfer and gene therapy using the viral vector system,

BACKGROUND ART

Non-proliferative (non-replicating) recombinant lentiviral vectors are used in a number of studies as a vector for gene therapy to treat various diseases, such as in a system which transports a target gene to a non-dividing cell in the central nervous system (CNS) and maintains its expression over a long period of time (Non-Patent Literatures 1-4). In particular, a primate lentiviral vector from HIV-1 (human immunodeficiency virus type 1) is the most proven vector for gene therapy (Non-Patent Literatures 5-8). However, it is well known that the lentiviral vector has a risk of inducing cancer because it will be integrated into chromosomes. Especially, cases have been reported where leukemia developed in the gene therapy of haematologic diseases. It has been therefore desired to selectively transfer the gene into the neurons in order to reduce the risk of occurrence of cancer and to develop a safer vector system in the gene therapy of nervous diseases.

On the other hand, for gene therapy of a certain cranial nerve disease, useful is a viral vector which can infect a nerve terminal, is retrogradely transported through an axon and introduce a target gene into a cell body in a target site located far from the infected site (FIG. 1).

To date, a retrograde transport system in the brain of cynomolgus monkey was developed using a recombinant HIV-1 virus which uses (is pseudotyped by) a vesicular stomatitis virus (VSV) glycoprotein (VSV-G) as an envelope glycoprotein (an envelope gene protein), but the retrograde transportation of the vector was not efficient (Non-Patent Literature 9). In the method described in the reference, very few cells in the central nervous system were retrogradely infected with the recombinant HIV-1 virus injected into the striatum of the monkey, as indicated by immunostaining.

On the other hand, rabies virus (RV) is known to have an activity that RV infects a synapse terminal, and is retrogradely transported through an axon. Indeed, there is a report that a retrograde transportation ability of a non-primate lentiviral vector based on equine anemia virus was promoted by RV-G (Non-Patent Literatures 10 and 11, and Patent Literature 1).

Further, HIV-1 lentivirus pseudotyped by RV-G has been reported (Non-patent Literature 3), but, in that report, an animal experiment (in vivo) was not actually conducted using that viral vector. In addition, gene transfer in CNS with a HIV-1 vector pseudotyped by a glycoprotein from Mokola lyssavirus, a neurotropic virus causing rabies, or VSV-G, has been studied. As a result of the nasal injection of the HIV-1 vector pseudotyped by the Mokola lyssavirus glycoprotein or VSV-G into a rat, these vectors were mutually comparable with regard to retrograde transportation to the olfactory nerve system (Non-Patent Literature 12). In addition, in that literature, an example in which a viral vector was administered through striatum was not described.

To date, the present inventors have revealed that highly-frequent retrograde gene transfer at various regions in the brain can be feasible by preparing a HIV-1 lentivirus vectors pseudotyped by rabies virus glycoprotein gene (RV-G) (RV-G/HIV-1 vector) (Patent Literature 2, Hum. Gene Ther., 2007). Furthermore, said inventor prepared the fused glycoprotein (FuG-B) wherein an intracellular domain of RV-G was replaced by that of VSV-G, and succeeded in constructing a lentiviral vector system that had a higher titer (functional titer) while sustaining an excellent (highly efficient) retrograde transport ability so as to significantly increase the frequency of retrograde gene transfer or introduction (Hum. Gene Ther., 2010).

REFERENCE LIST

Patent Literature

Patent Literature 1: National Publication of International Patent Application No. 2004-517057

Patent Literature 2: Japanese Patent Laid-Open No. 2009-34029

Non Patent Literature

Non-Patent Literature 1: NALDINI, L., BLÖMER, U., GAGE, F. H., TRONO, D., and VERMA, I. M. (1996). Efficient transfer, integration, and sustained long-term expression of the transgene in adult rat brains injected with a lentiviral vector. Proc. Natl. Acad. Sci. USA 93, 11382-11388.

Non-Patent Literature 2: REISER, J., HARMISON, G., KLUEPFEL-STAHL, S., BRADY, R. O., KARLSSON, S., and SCHUBERT, M. (1996). Transduction of nondividing cells using pseudotyped defective high-titer HIV type 1 particles. Proc. Natl. Acad. Sci. USA 93, 15266-15271.

Non-Patent Literature 3: MOCHIZUKI, H., SCHWARTZ, J. P., TANAKA, K., BRADY, R. O., and REISER, J. (1998). High-titer human immunodeficiency virus type 1-based vector systems for gene delivery into nondividing cells. J. Virol. 72, 8873-8883.

Non-Patent Literature 4: MITROPHANOUS, K. A., YOON, S., ROHLL, J. B., PATIL, D., WILKES, F. J., KIM, V. N., KINGSMAN, S. M., KINGSMAN, A. J., and MAZARAKIS, N. D. (1999). Stable gene transfer to the nervous system using a non-primate lentiviral vector. Gene Ther. 6, 1808-1818.

Non-Patent Literature 5: KORDOWER, J. H., EMBORG, M. E., BLOCH, J., MA, S. Y., CHU, Y., LEVENTHAL, L., MCBRIDE, J., CHEN, E.-Y., PALFI, S., ROITBERG, B. Z., BROWN, W. D., HOLDEN, J. E., PYZALSKI, R., TAYLOR, M. D., CARVEY, P., LING, Z., TRONO, D., HANTRAYE, P., DÉGLON, N., and AEBISCHER, P.

(2000). Neurodegeneration prevented by lentiviral vector delivery of GDNF in primate models of Parkinson's disease. Science 290, 767-773.

Non-Patent Literature 6: MARR, R. A., ROCKENSTEIN, E., MUKHERJEE, A., KINDY, M. S., HERSH, L. B., GAGE, F. H., VERMA, I. M., and MASLIAH, E. (2003). Neprilysin gene transfer reduces human amyloid pathology in transgenic mice. J. Neurosci. 23, 1992-1996.

Non-Patent Literature 7: ROSENBLAD, C., GEORGIEVSKA, B., and KIRIK, D. (2003). Long-term striatal overexpression of GDNF selectively downregulates tyrosine hydroxylase in the intact nigrostriatal dopamine system. Eur. J. Neurosci. 17, 260-270.

Non-Patent Literature 8: LO BIANCO, C., SCHNEIDER, B. L., BAUER, M., SAJADI, A., BRICE, A., IWATSUBO, T., and AEBISCHER, P. (2004). Lentiviral vector delivery of parkin prevents dopaminergic degeneration in an α-synuclein rat model of Parkinson's disease. Proc. Natl. Acad. Sci. USA 101, 17510-17515.

Non-Patent Literature 9: KITAGAWA, R., MIYACHI, S., HANAWA, H., TAKADA, M., and SHIMADA, T. (2007). Differential characteristics of HIV-based versus SIV-based lentiviral vector systems: gene delivery to neurons and axonal transport of expressed gene. Neurosci. Res. 57, 550-558.

Non-Patent Literature 10: MAZARAKIS, N. D., AZZOUZ, M., ROHLL, J. B., ELLARD, F. M., WILKES, F. J., OLSEN, A. L., CARTER, E. E., BARBER, R. D., BABAN, D. F., KINGSMAN, S. M., KINGSMAN, A. J., O'MALLEY, K., and MITROPHANOUS, K. A. (2001). Rabies virus glycoprotein pseudotyping of lentiviral vectors enables retrograde axonal transport and access to the nervous system after peripheral delivery. Human Mol. Genet. 10, 2109-2121.

Non-Patent Literature 11: AZZOUZ, M., RALPH, G. S., STORKEBAUM, E., WALMSLEY, L. E., MITROPHANOUS, K. A., KINGSMAN, S. M., CARMELIET, P., and MAZARAKIS, N. D. (2004). VEGF delivery with retrogradely transported lentivector prolongs survival in a mouse ALS model. Nature 429, 413-417.

Non-Patent Literature 12: DESMARIS, N., BOSCH, A., SALAÜN, C., PETIT, C., PRÉVOST, M.-C., TORDO, N., PERRIN, P., SCHWARTZ, O., DE ROCQUIGNY, H., and HEARD, J. M. (2001). Production and neurotropism of lentivirus vectors pseudotyped with lyssavirus envelope glycoproteins. Mol. Ther. 4, 149-156.

SUMMARY OF INVENTION

Technical Problem

Since the prior RV-G vector and FuG-B vector have the feature to transfer the gene into both neurons and glia cells at an injected site, the gene would be therefore introduced not only into the neurons but also into dividing cells.

Therefore, an object of the present invention is to provide a much safer lentiviral vector system that enables not only the gene transfer via a retrograde transportation with a higher frequency, but also selective or specific gene transfer into the neurons while reducing the efficiency of gene transfer into the dividing cells such as neural stem cells and glia cells so as to reduce the risk of occurrence of cancer.

Solution to Problems

The present inventor has found that the above problem can be solved by pseudotyping the lentiviral vector by means of a fused polypeptide as an envelope comprising a fused extracellular domain consisting of the N-terminal region of an extracellular domain of rabies virus glycoprotein (RV-G) and the C-terminal region of an extracellular domain of vesicular stomatitis virus glycoprotein (VSV-G), a transmembrane domain of RV-G or VSV-G, and an intracellular domain of VSV-G;

That is, the present invention relates to the following aspects.

[Aspect 1]

A kit for preparing a retrograde transport viral vector comprising:

(1) a packaging plasmid containing the gag gene and the pol gene of HIV-1;

(2) a packaging plasmid containing an accessory gene of HIV-1;

(3) a transfer plasmid containing an target gene (a transgene); and (4) an envelope plasmid containing, as an envelope gene, a gene encoding a fused polypeptide comprising a fused extracellular domain consisting of the N-terminal region of an extracellular domain of rabies virus glycoprotein (RV-G) and the C-terminal region of an extracellular domain of vesicular stomatitis virus glycoprotein (VSV-G), a transmembrane domain of RV-G or VSV-G, and an intracellular domain of VSV-G.

[Aspect 2]

A kit for preparing a producer cell comprising the kit for preparing a viral vector according to Aspect 1, and a host cell.

[Aspect 3]

A method of producing a producer cell, comprising: cotransfecting an infected cell with the packaging plasmid, the transfer plasmid, and the envelope plasmid, comprised in the kit for preparing a viral vector according to Aspect 1.

[Aspect 4]

A producer cell obtained by the method of producing a producer cell according to Aspect 3.

[Aspect 5]

A method of producing a viral vector, comprising: culturing the producer cell according to Aspect 4 and harvesting virus particles from the supernatant of the culture.

[Aspect 6]

A viral vector possessing a neuron-specific retrograde transportation ability, produced by the method of producing a viral vector according to Aspect 5.

[Aspect 7]

A method of gene transfer, comprising: infecting a nerve terminal of an animal with the viral vector according to Aspect 6; introducing the viral vector specifically into a cell body of the nerve at a target region in the brain by retrograde transportation of the viral vector through an axon of the nerve; and expressing a target gene in the cell body.

[Aspect 8]

An agent for gene therapy containing the viral vector according to Aspect 6 as an active ingredient.

[Aspect 9]

A method of gene therapy for a brain disease, comprising; integrating a target gene introduced by the method according to Aspect to 7 into the chromosome of a cell in a target region to express it.

[Aspect 10]

An envelope for pseudotyping a lentiviral vector, consisting of a fused polypeptide comprising a fused extracellular domain consisting of the N-terminal region of an extracellular domain of rabies virus glycoprotein (RV-G) and the C-terminal region of an extracellular domain of vesicular stomatitis virus glycoprotein (VSV-G), a transmembrane domain of RV-G or VSV-G and the intracellular domain of vesicular stomatitis virus glycoprotein (VSV-G).

[Aspect 11]

A gene encoding an envelope consisting of the fused polypeptide according to Aspect 10.

[Aspect 12]

A envelope plasmid comprising the gene encoding an envelope consisting of the fused polypeptide according to Aspect 11.

BRIEF DESCRIPTION OF THE DRAWINGS

FIG. 7 shows the base sequence (nucleotide sequence) encoding the envelope according to the present invention (SEQ ID NO: 1), which is contained in the envelope plasmid pCAG-FuG-C (SEQ ID NO: 5).

DETAILED DESCRIPTION

Advantages of the Invention

Figure 1:
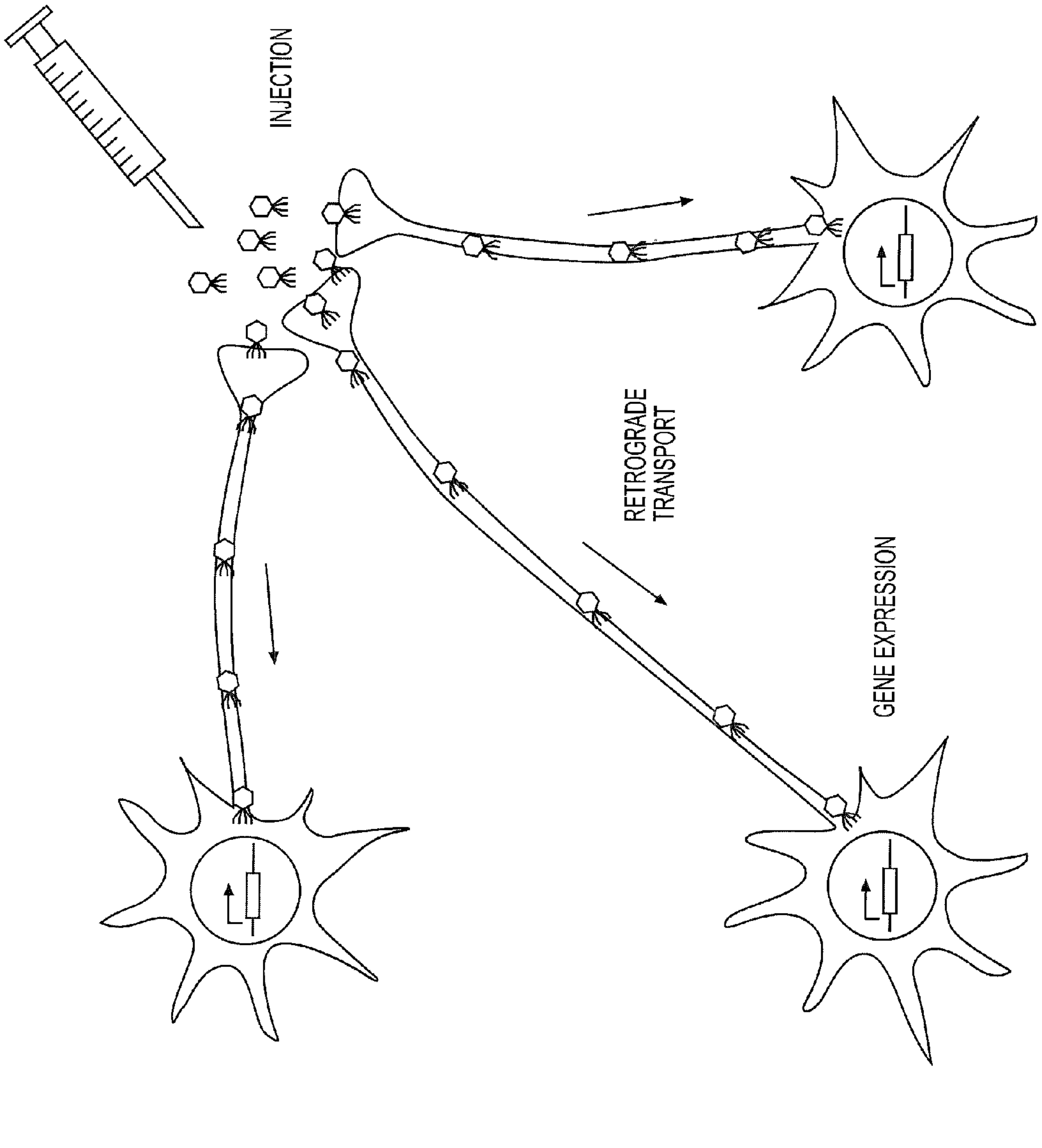
FIG. 1 shows a schematic overview of a HIV-1-pseudotype vector exhibiting highly-frequent retrograde transportation.

The present invention demonstrates, in vivo, that in an animal including mammals such as mice, by injecting a recombinant viral vector containing a specific gene for transfection at a region of the brain where a nerve terminal (a synapse terminal) is present, and by allowing the viral vector to be retrogradely transported through an axon, the target gene (the transgene) can be efficiently and specifically (selectively) introduced for expression into the neuron that is a non-dividing cell in the central nervous system distant from the infected (injected) site of the viral vector. In particular, by using a kit for preparing a viral vector which utilizes a specific packaging plasmid, transfer plasmid and envelope gene, a viral vector having an unexpectedly higher virus titer can be obtained, and a recombinant viral vector showing a highly-frequent and neuron-specific retrograde transportation ability in the brain can be advantageously produced.

The viral vector possessing a neuron-specific retrograde transportation ability according to the present invention suppresses the frequency of gene transfer into the dividing cells such as neural stem cells and glia cells. As a result, the risk of occurrence of cancer can be reduced, and any side effects caused by the gene transfer and expression in other cells than the neurons can be decreased.

DESCRIPTION OF EMBODIMENTS

The viral vector according to the present invention is the neuron-specific retrograde transport vector (NeuRet), which is characterized by having a high titer. The vector may be prepared by means of a kit comprising:

(1) a packaging plasmid containing the gag gene and the pol gene of HIV-1;

(2) a packaging plasmid containing an accessory gene of HIV-1;

(3) a transfer plasmid containing an target gene (a transgene); and (4) an envelope plasmid containing, as an envelope gene, a gene encoding a fused polypeptide comprising a fused extracellular domain consisting of the N-terminal region of an extracellular domain of rabies virus glycoprotein (RV-G) and the C-terminal region of an extracellular domain of vesicular stomatitis virus glycoprotein (VSV-G), a transmembrane domain of RV-G or VSV-G, and an intracellular domain of VSV-G.

In the kit for preparing the viral vector according to the present invention, "gag" is a gene which encodes retroviral core proteins, and "pol" is a gene which encodes reverse transcriptase and the like. In addition, an "envelope gene" is a gene which encodes an envelope, a virus specific protein which is located in an envelope that is an outer membrane of a retrovirus comprised of a lipid bilayer membrane. The envelope plays an important role for a virus to adhere to and invade into a cell. Further, an "accessories gene" means, for example, the rev gene which regulates the expression of structural genes.

A preferred and representative example of the kit for preparing a viral vector according to the present invention is characterized by the use of "pCAGkGP1.1R" and "pCAG4-RTR2" as (1) a packaging plasmid containing the gag and the pol gene of HIV-1 and (2) a packaging plasmid containing an accessories gene of HIV-1 respectively, and further by the use of "pCL20 c-MSCV-X as a transfer plasmid where "X" represents a target gene. The target gene "X" to be transfected is encoded downstream of a mouse stem cell virus promoter in the above transfer plasmid.

Each plasmid contained in the above kit for preparing a viral vector is constructed based on a HIV-1 vector system "SJ1" developed by Dr. Arthur Nienhuis at St. Jude Children's Research Hospital (HANAWA, H., et al., (2002) Mol. Ther. 5, 242-251; (2004). Blood 103, 4062-4069. Supplied by St. Jude Children's Research Hospital). This vector system is known to show an about 10-fold greater titer in HeLa cells than other vector systems. Therefore, those skilled in the art can readily produce each of these plasmids by referring to the specification of the present application and the above references. Note that the above (1) and (2) of the packaging plasmids may be constructed as one plasmid.

The envelope gene contained in the envelope plasmid of the kit for preparing the viral vector according to the present invention encodes the fused polypeptide comprising a fused extracellular domain consisting of the N-terminal region of the extracellular domain of rabies virus glycoprotein (RV-G) and the C-terminal region of an extracellular domain of vesicular stomatitis virus glycoprotein (VSV-G), the transmembrane domain of RV-G or VSV-G, and the intracellular domain of VSV-G. Note that at the fusion boundaries of each domain, one or more amino acids can be optionally altered by deletion, insertion, substitution, or the like, and all of the amino acids constituting each domain are not necessarily included.

Examples of the envelope gene can include an envelope gene encoding a polypeptide consisting of, for example, about 420 amino acids or more, or 430 amino acids or more of the N terminal region of the extracellular domain of RV-G originally consisting of 458 amino acids as the N terminal region constituting the fused extracellular domain.

As a preferred example, there may be mentioned an envelope gene encoding the amino acid sequence shown in SEQ ID NO: 2 (FuG-C), and preferably a nucleic acid molecule having the base sequence of 1~1,365 bases from N terminal shown in SEQ ID NO: 1 (FIG. 7) wherein the 1~1,317 bases (including start codon) at the 5' side are originated from RV-G and the 1,318~1,365 bases at the 3' side are originated from VSV-G. Given the codon degeneracy, the above base sequences can be optionally altered to optimize the codon along with other elements in the envelope plasmid. SEQ ID NOs: 4 and 3 show examples of the amino acid sequence of rabies virus glycoprotein (RV-G) and the base sequence encoding thereof.

Thus, the above fused polypeptide is effective as an envelope to pseudotype various kinds of lentiviral vectors, in particular a HIV-1 lentiviral vector. Therefore, the present invention also relates to an envelope for pseudotyping a lentiviral vector comprising the above fused polypeptide, a gene encoding an envelope comprising the above fused polypeptide, and an envelope plasmid itself containing the above gene. In each of the plasmids contained in the kit for preparing a viral vector according to the present invention, each gene is linked under expression control of any expression regulatory sequences known to persons skilled in the art.

The phrase "under expression control of" means DNA encoding a given amino acid sequence has the ability to express a protein having that amino acid sequence under given conditions. In case that DNA encoding a given amino acid sequence is linked under expression control of an expression regulatory sequence, that DNA will express a given protein under given conditions. The term "an expression regulatory sequence" herein means a nucleic acid sequence that regulates expression of other nucleic acid sequences, and it regulates and modulates transcription and preferably even translation of other nucleic acid sequences. Expression regulatory sequences include an appropriate promoter, an enhancer, a transcription terminator, the start codon (namely, ATG) in a gene encoding a protein, a splicing signal for intron, a polyadenylation site and the stop codons.

The term "a promoter" means an essential sequence for transcription. Promoters also include promoter elements that regulate gene expression cell-type specifically, tissue specifically, or promoter-dependently via a signal or a modulator from the outside. A promoter element is linked at either the 5' or 3' region of DNA to be expressed. In addition, promoters include any of those constitutive or inducible. Promoters known for persons skilled in the art can be selected accordingly, depending on the classes of target genes and viral vectors to be used, the kinds of animals and brain diseases to be treated, pathological conditions of patients, and so on.

For example, in the envelope plasmid according to the present invention, an envelope gene is preferably linked such that it will be expressed under control of the cytomegalovirus enhancer and the avian β actin promoter. Such an envelope plasmid can be obtained by replacing, in accordance with the standard method, the base sequence encoding an extracellular domain and a transmembrane domain of vesicular stomatitis virus glycoprotein (VSV-G) with the base sequence encoding an extracellular domain and a transmembrane domain in the nucleic acid (cDNA) encoding a glycoprotein from a CVS strain of rabies virus (RV-G) which is passed in the brain of an infected infant mouse (provided by Dr. Kinjiro Morimoto at National Institute of Infectious Diseases) (Morimoto, K. et al., (1998) Proc Natl. Acad. Sci., USA 95, 3152-3156: SEQ ID NO 3) in the envelope plasmid "pCAGGS-VSV-G" included in the above vector system "SJ1". Therefore, persons skilled in the art can readily produce these plasmids described above by referring to the specification of the present application and the above references. Note that the glycoprotein (RV-G) of the rabies virus CVS strain is not limited to those having the base sequence shown in SEQ ID NO 3 above, but glycoproteins (RV-G) from any strains of any known rabies viruses can be used.

A target gene contained in a transfer plasmid known for persons skilled in the art can selected accordingly, depending on the intended use of a viral vector, the kinds of animals and brain diseases to be treated, pathological conditions of patients, and so on. Therefore, they include various genes of mammal, such as mouse, monkey and human, for example, a gene required for survival or protection of nigrostriatal system, which is used to treat cranial nerve diseases or neurodegenerative diseases represented by Parkinson's disease, etc. (for example, tyrosine hydroxylase, a neurotrophic factor from an glial cell line), or genes such as the interleukin-2 receptor α subunit (a target molecule of a recombinant immunotoxin) for research on cranial nerve systems and a light dependent ion channel, etc.

Host cells contained in the kit for producing a producer cell according to the present invention have no particular limitation as long as they can be infected by the above kit for preparing a viral vector so that they can produce a cell called "a producer cell" which can produce a retroviral particle. Any cells known to persons skilled in the art, for example, commercially available appropriate animal cells such as HEK293 T-cells (SV40 large T antigen is introduced) can be used.

Depending on their composition, intended use, etc., in addition to each of the above plasmids and/or host cells, the various kits according to the present invention can optionally contain other elements or ingredients known to persons skilled in the art, such as various reagents, buffers, various adjuvants, reaction plates (containers) and the like.

Using the kit for preparing a producer cell according to the present invention, a producer cell can be produced by co-transfecting an infected cell with a packaging plasmid, a transfer plasmid and an envelope plasmid contained in the kit for preparing a viral vector. This transfection is transient and can be performed by any methods known to persons skilled in the art, such as the calcium phosphate method.

A viral vector having a neuron-specific or neuron-selective retrograde transport ability and a high titer in the brain can be produced by culturing the resultant producer cells using any methods or means known to persons skilled in the art, and harvesting virus particles from the culture supernatant.

A nerve terminal can be infected with the viral vector according to the invention, and the retrograde transportation of the viral vector through an axon of that nerve can specifically or selectively introduce the viral vector into a cell body of that nerve at the target region in the brain, and a target gene can be expressed in the cell body. Target regions in the brain include primary motor cortex, primary somatosensory cortex, parafascicular nucleus of thalamus and substantia nigra pars compacta, which are projecting to striatum, and the brain center such as piriform cortex, subiculum, amygdala basolateral nucleus, anterior paraventricular nucleus, mediodorsal nucleus of thalamus and lateral hypothalamus, which are projecting to ventral striatum (nucleus accumbens). Further, the viral vector according to the present invention is retrogradely transported through an axon of motor neuron in the spinal cord.

Therefore, the viral vector according to the present invention is effective as an active ingredient of an agent for gene therapy. The agent for gene therapy can contain, in combination with the active ingredient, any pharmaceutically acceptable careers or diluents or other components known to those skilled in the art.

The effective amount of the active ingredient according to the present invention can be selected accordingly by persons skilled in the art, depending on the classes of the transgene contained in the viral vector; the kinds and seriousness of brain diseases or neurodegenerative disorders; therapeutic strategy; age, body weight, sex, general health of patient; and racial (genetic) background of patient. A dose of the active ingredient (the viral vector) can be, for example, a total amount of $10^8$ to $10^9$ TU (Transducing Unit) per administration for several infection (injection) sites. Note that the viral vector or the agent for gene therapy can be infected (injected) at a predetermined site in a patient using any administration methods or devices known to those skilled in the art.

By administering the viral vector according to the present invention to a patient, a gene introduced into a predetermined cell in a target region will be integrated into the chromosome of that cell, and the target gene will be stably expressed. Therefore, the present method of gene transfer can be used to perform gene therapy for brain diseases, neurodegenerative diseases (for example, Parkinson's disease) or the like of mammals including primate such as human.

Now, the present invention will be described in detail by Examples and test examples. These examples represent a part of the present invention, and the technical scope of the present invention is not limited at all by these Examples. Unless otherwise stated, experimental conditions and the like in each procedure were according to the methods described in the references cited herein, or the standard methods in the art.

Example 1

Preparing a Viral Vector

A viral vector according to the present invention was prepared using a HIV-1 vector system developed by Dr. Arthur Nienhuis at St. Jude Children's Research Hospital. Namely, a packaging plasmid containing the gag and pol gene (pCAGkGP1.1R), a packaging plasmid containing an accessories gene (pCAG4-RTR2) and a transfer plasmid containing a green fluorescence protein (GFP) as a target gene (pCL20 c-MSCV-GFP) were used.

Figure 2:
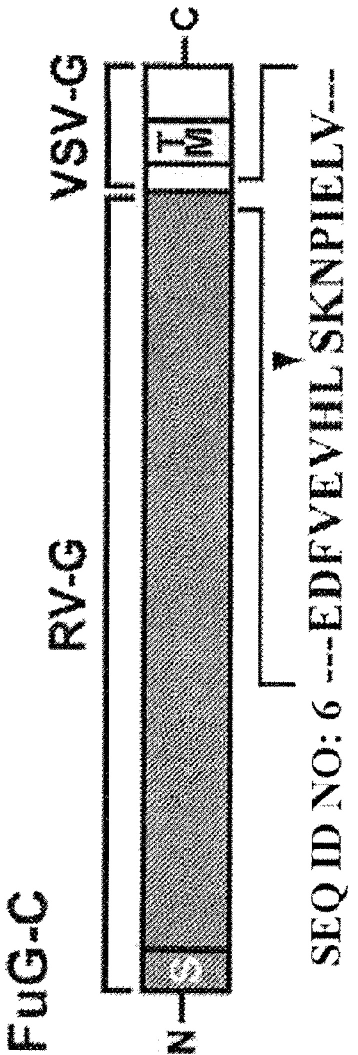
FIG. 2 shows the structure of FuG-C wherein the C-terminal region of an extracellular domain of vesicular stomatitis virus glycoprotein (VSV-G) is linked to the N-terminal region of an extracellular domain of rabies virus glycoprotein (RV-G). It also comprises a transmembrane domain and an intracellular domain of VSV-G. The linking site between the extracellular domains of RV-G and VSV-G is indicated by an arrow, and amino acids in this boundary region (SEQ ID NO: 6) are also shown. "S" means a signal peptide, and "TM" means a transmembrane domain.

As an envelope plasmid (pCAG-FuG-C), a vector containing a base sequence (SEQ ID NO 5) encoding an envelope was produced according to the conventional method, wherein the envelope was a fused glycoprotein (FuG-C) consisting of the C-terminal region of the extracellular domain of VSV-G linked to the N-terminal region of the extracellular domain of RV-G that had been provided by Dr. Kinjiro Morimoto at National Institute of Infectious Diseases, and the transmembrane domain and the intracellular domain of VSV-G. (FIG. 2). The extracellular domain of FuG-C consisted of 439 amino acids from the N-terminal region of the extracellular domain of RV-G and 16 amino acids from the C-terminal region of the extracellular domain of VSV-G. Similarly, viral vectors comprising VSV-G and RV-G, respectively, were prepared for the purpose of comparison.

Determination of Viral Titer:

HEK293 T-cells (eighteen 10-cm dish) were transfected with a viral vector solution containing these plasmids using the calcium phosphate method. After cultured for 48 hours, virus particles were harvested from the culture supernatant and centrifuged, which was filtered with a 0.45-μm cellulose filter. Then, the vector particles were collected by centrifugation (10,000×g, 16 to 18 hours), and suspended in PBS (1 ml). The suspension was subjected to Sepharose Q FF ion exchange column chromatography, which was washed with PBS and then eluted using a linear gradient from 0 to 1.5 M NaCl. Fractionations were monitored by the absorbance at 260/280 nm. Fractionations containing the vector particles were collected, concentrated using an ultrafiltration filter, and stored at −80° C.

In order to evaluate a viral titer, the following culture cells that were easily available from the public depositories and the like were plated to a 6-well cell culture plate (MULTIWELL (R), FALCON) to infect the cultured cells with an appropriate concentration of the virus solution: Human renal cell: HEK293 T (available from a cell bank of RIKEN, Accession No: RCB2202), mouse neuroblast: Neuro2A (available from ATCC, ID No: CCL-131TM), mouse neuroblast: N1E-115 (available from ATCC, ID No: CRL-2263TM).

Titers were measured using FACS Calibur (Nippon Becton Dickinson Co., Tokyo, Japan) (FIG. 2B). Then, the amount of RNA contained in vector stock was measured using a quantitative RT-PCR method.

The results are shown in Table 1 below. Although the functional titer of FuG-C vector was detected only in Neuro2A, its value was significantly decreased compared to that of VSV-G or RV-G vector (ANOVA, Tukey HSD, $p<0.01$), and the RNA titer of FuG-C was comparable to that of VSV-G or RV-G vector.

TABLE 1

Titer of lentiviral vectors

| | Functional titer | | | |
|---|---|---|---|---|
| | HEK293T | Neuro2A | N1E-115 | RNA titer |
| VSV-G | $1.0 \pm 0.02 \times 10^9$ | $5.0 \pm 0.1 \times 10^8$ | $2.8 \pm 0.1 \times 10^8$ | $6.8 \pm 0.6 \times 10^9$ |
| RV-G | $5.2 \pm 1.0 \times 10^7$ | $1.9 \pm 0.04 \times 10^7$ | $3.4 \pm 0.2 \times 10^6$ | $8.6 \pm 0.7 \times 10^9$ |
| FuG-C | ND | $1.2 \pm 0.01 \times 10^6$ * | ND | $8.9 \pm 0.8 \times 10^9$ |

ND, Not detected.

* $P < 0.01$ vs VSV-G or RV-G (ANOVA, Tukey HSD)

Example 2

Introduction of the Viral Vector into the Brain of Mouse

Animal care and use was performed according to a guideline by the animal care and use committee of Fukushima Medical University. A 12-week old mouse (C57BL/6J) was anesthetized with pentobarbital sodium (50 mg/kg, i.p.), and a solution containing a vector produced as described above ($4.8\times10^{10}$ copies/ml) was injected in the brain (striatum) of the mouse using a brain stereotaxic apparatus. The injection was performed according to the mouse brain atlas (PAXINOS, G., and FRANKLIN, K. B. J. (2001). The Mouse Brain in Stereotaxic Coordinates, 2nd edn. (Academic Press, San Diego). 2 μl of the solution was injected (0.1 μl/min) at two points along the track respectively in the dorsal region of striatum through a glass microinjection capillary connected to a microinjection pump. Anteroposterior, mediolateral and dorsoventral coordinates from bregma were 0.50, 2.00 and 2.50/3.25 (mm), respectively.

Four weeks after the injection, a mouse was deeply anesthetized with pentobarbital sodium (50 mg/kg, i.p.), and then the brain was perfused and fixed with 4% formalin and 0.1 M phosphate buffer (PB: pH 7.4) via the heart before extirpating the brain. Sections were prepared using a cryostat and analyzed using the immunostaining method.

Figure 3:
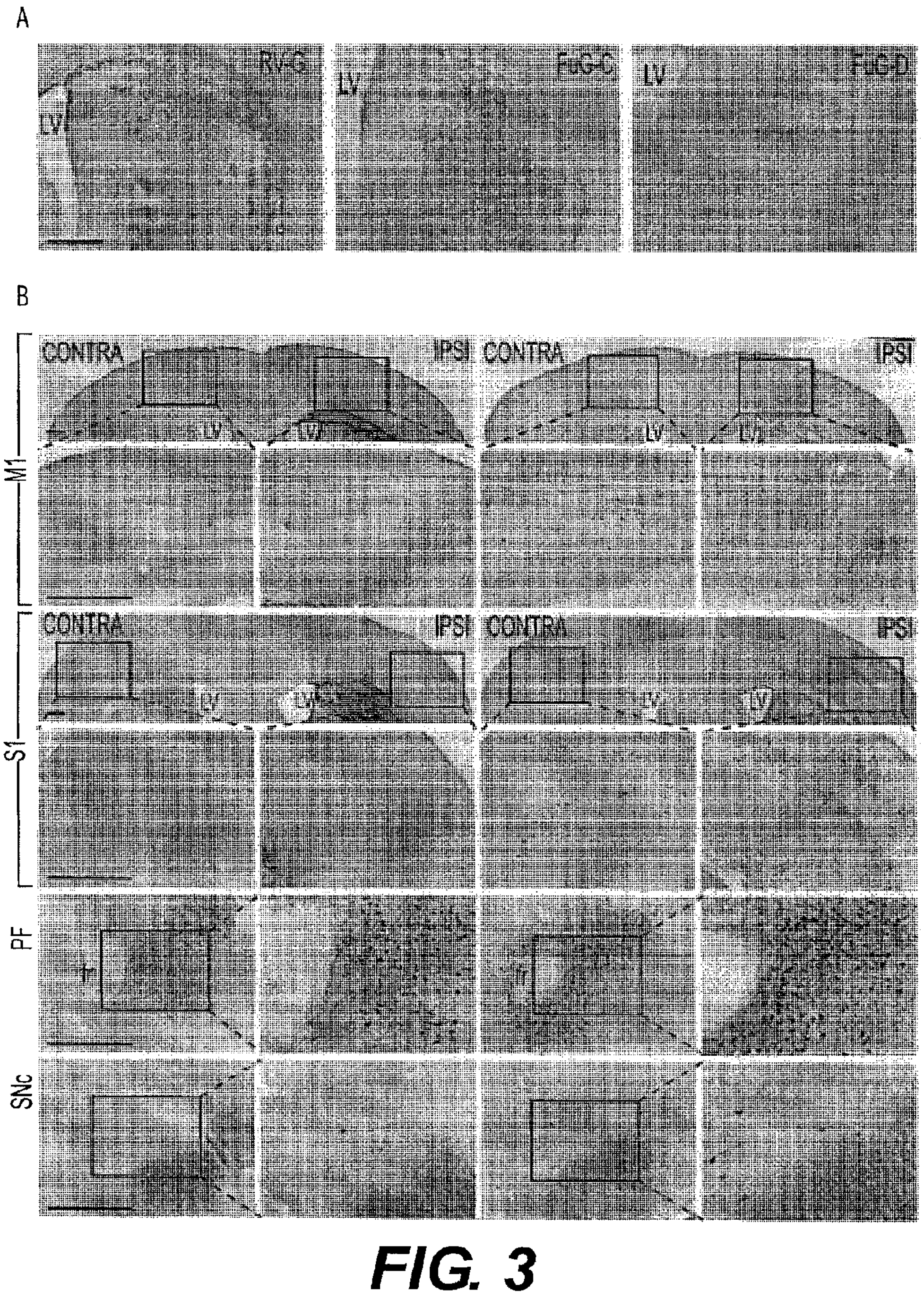
FIG. 3 shows photographs of an expression pattern of the transgene: (A) The expression pattern at striatum. (B) The expression pattern of the transgene via the retrograde transportation by RV-G and FuG-C vectors in primary motor cortex (M1), primary somatosensory cortex (S1), parafascicular nucleus of thalamus (PF), substantia nigra pars compacta (SNc), fr (habenulointerpeduncular tract); SNr (substantia nigra rope state par); LV (lateral ventricle). Scale bar: 500 μm.

Although immuno-positive signals were observed in a wide range of the striatum of the mouse that received the injection of the FuG-C vector, their intensity had been significantly decreased compared to those of RV-G vectors (FIG. 3A). In addition, the expression of the transgene was analyzed by the immunostaining method in primary motor cortex (M1), primary somatosensory cortex (S1), parafascicular nucleus of thalamus (PF) and substantia nigra pars compacta (SNc), which are representative brain regions projecting to striatum. Both the same and opposite regions of the brain cortex as the injected site, and in the same region of PF and SNc in the brain as the injected side were observed (FIG. 3B), and the number of the positive cells in each region was counted (Table 2). The efficiency of transfer of the gene with the FuG-C vector was significantly increased in all of the regions in the brain when compared to that with the RV-G vector (Student t-test, $p<0.01$ or 0.05). These data indicate that the FuG-C vector has improved the efficiency of transfer of the gene to the neurons via the retrograde transport.

Example 3

Selective Transfer of Gene into Neurons

Figure 5:
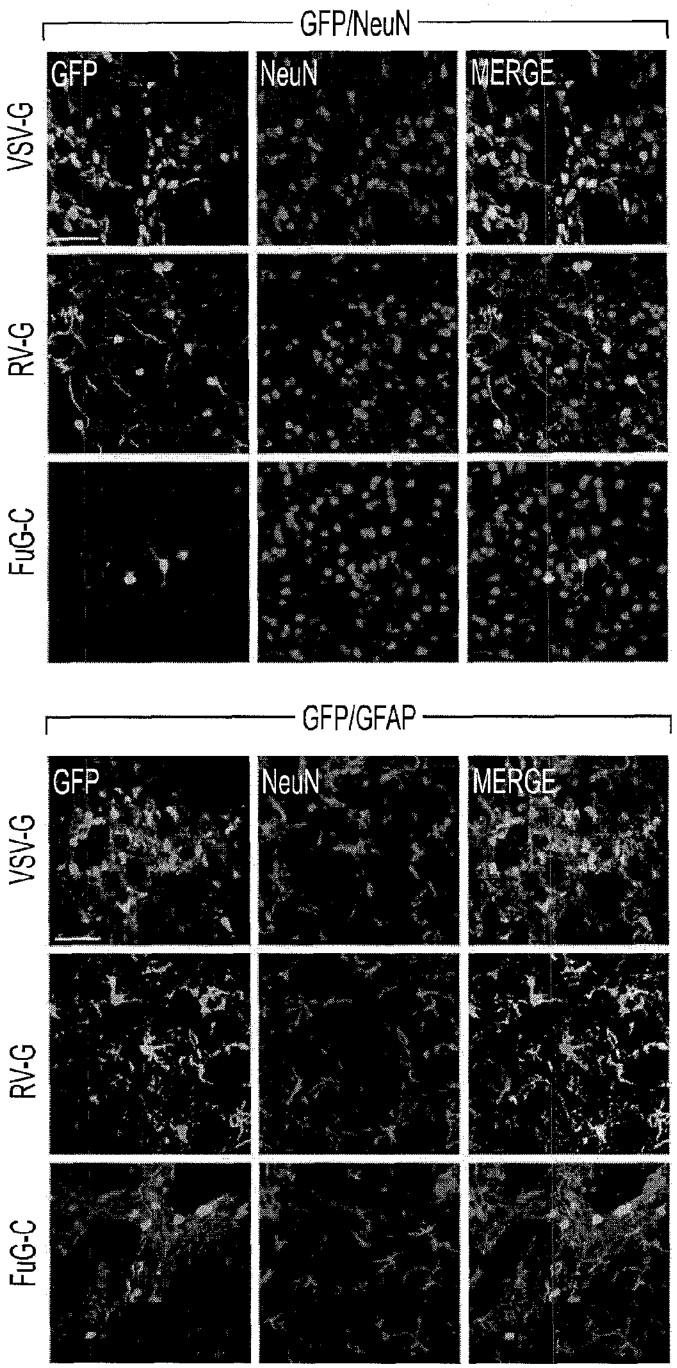
FIG. 5 shows photographs with a confocal microscope of the efficiency of the gene transfer into the neurons and glia cells at an injected site. Scale bar: 50 μm.

The efficiency of the gene transfer into the neurons and glia cells at the injected site of the FuG-C vector was analyzed. After each vector of VSV-G, RV-G and FuG-C ($1.2\times10^{10}$ copies/ml) was injected into the striatum of the mouse, the sections of the striatum were prepared in the same way as in Example 2. Double immunostaining was done with the neuron marker of NeuN and GFP, or with the glia cell marker of GFAP and GFP (FIG. 5). First, a ratio of the number of $GFP^+/NeuN^+$ double positive cells to the number of the total $NeuN^+$ positive cells, and a ratio of the number of $GFP^+/GFAP^+$ double positive cells to the number of the total $GFAP^+$ positive cells were measured, respectively. The ratio of the number of $GFP^+/NeuN^+$ double positive cells was 81.7±2.9%, 21.4±1.8%, and 6.2±1.4% for the vectors of VSV-G, RV-G and FuG-C, respectively (n=4). The efficiency of the gene transfer with the FuG-C vector into the neurons in the striatum was significantly decreased compared to those with the other vectors (ANOVA, Tukey HSD, $p<0.001$ vs VSV-G, $p<0.01$ vs RV-G). On the other hand, the ratio of the number of $GFP^+/GFAP^+$ double positive cells was 5.9±0.7%, 71.5±3.6%, and 0.3±0.03% for the vectors of VSV-G, RV-G and FuG-C, respectively (n=4). Thus, almost no gene transfer into the glia cells was observed in the case of the FuG-C vector, showing that the FuG-C vector can transfer the gene selectively into the neurons mainly via the retrograde transportation.

Example 4

Properties of the Transfer of Gene with Vectors into Neural Stem Cells

It is known that the VSV-G vector has a high gene-transfer efficiency into neural stem cells. The properties of the vectors

TABLE 2

Efficiency of the retrograde transfer of gene with lentiviral vectors

| | Brain region | | | | | |
|---|---|---|---|---|---|---|
| | M1 | | S1 | | | |
| | Ipsi | Contra | Ipsi | Contra | PF | SNc |
| RV-G | 61.2 ± 9.0 | 10.4 ± 2.3 | 59.6 ± 8.6 | 9.1 ± 1.8 | 121.2 ± 13.6 | 2.0 ± 0.4 |
| FuG-C | 246.6 ± 20.5[b] | 67.1 ± 3.6 * | 248.8 ± 21.7 * | 50.8 ± 4.4 * | 191.6 ± 24.5** | 7.2 ± 0.7 * |

* P < 0.01,
**P < 0.05 vs RV-G (Student t-test)

Figure 4:
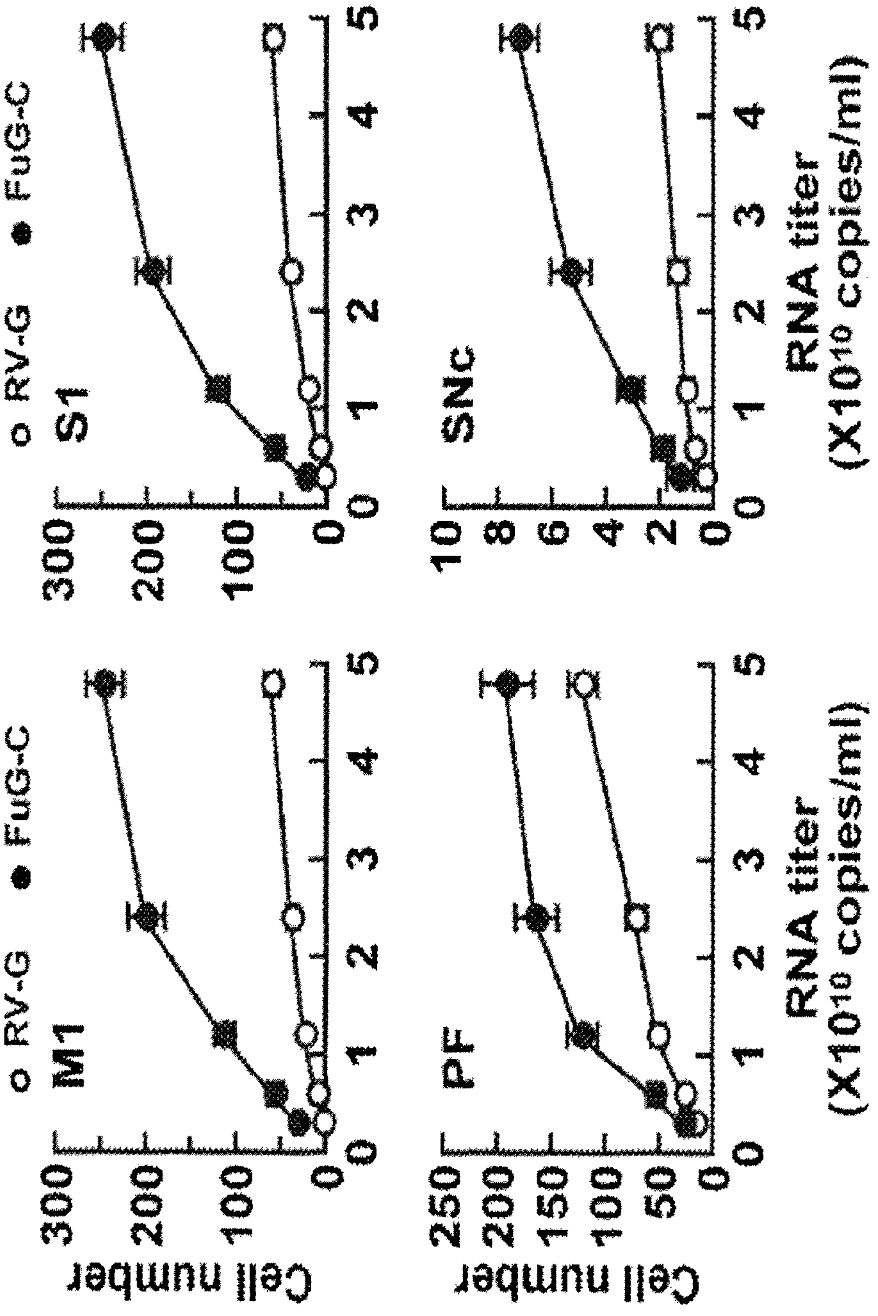
FIG. 4 shows graphs demonstrating titer-dependency of efficiency of the retrograde gene expression. (Two-way ANOVA: main effect of vector, $F_{(1,30)}=223.9$ for M1, 231.7 for S1, 46.5 for PF, and 87.7 for SNc, $P<0.001$ in all regions; and interaction between vector and titer, $F_{(4,30)}=20.4$ for M1, 21.7 for S1, 3.6 for PF, and 8.4 for SNc, $P<0.05$ in all regions).
Figure 6:
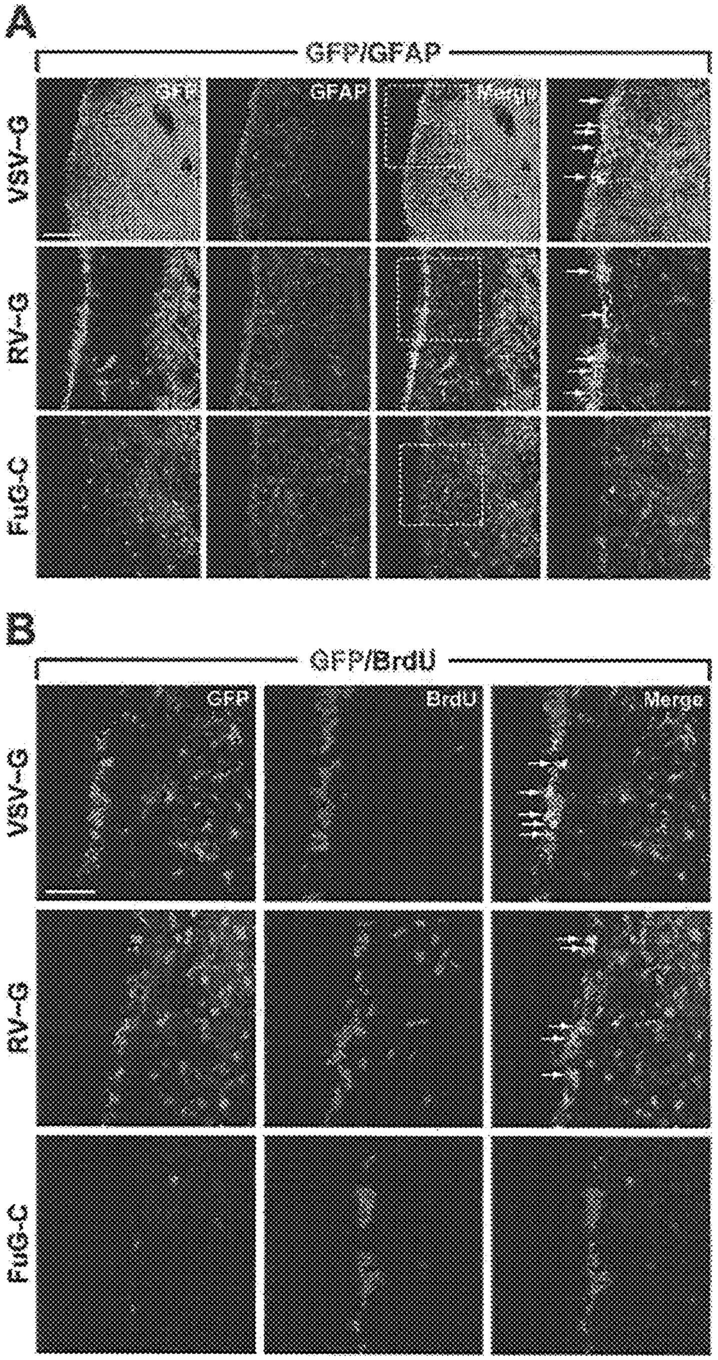
FIG. 6 shows photographs with a confocal microscope of the efficiency of the gene transfer into the neural stem cells. (A) Doublestaining with GFAP: (B) Doublestaining with BrdU. Arrows indicate representative double-stained cells. Scale bar: 100 μm (A), 50 μm (B).

Next, in order to confirm the improvement in the retrograde transfer of gene with the FuG-C vector, vector solution with various concentration of the vector ($3.0\times10^9$~$4.8\times10^{10}$ copies/ml) was injected into the mouse striatum, and the number of the positive cells was counted in M1, S1, PF and SNc (FIG. 4). The number of the positive cells clearly showed a concentration-dependent increase in every region in the case of the injection of the FuG-C vector. Although the concentration-dependent increase was also observed in the animals with the injection of the RV-G vector, its tendency was lower than that of the FuG-C vector (two-way ANOVA). These results show that the FuG-C vector enables the transfer of gene via the retrograde transport with a higher efficiency than the RV-G vector.

for the gene transfer into the neural stem cells localized in circumventricular region (SVZ) were analyzed. The viral vector solution ($1.2\times10^{10}$ copies/ml) was injected into the SVZ of the mouse, the brain sections were prepared, followed by double immunostaining using the neural stem cell marker of GFAP and GFP (FIG. 6A). Many GFAP positive cells were observed when the gene transfer was done with the injection of the VSV-G or the RV-G vector. On the other hand, almost no positive cell was observed in the case of the FuG-C vector. Furthermore, BrdU was administered to label dividing cells and the brain sections were prepared one week after in order to carry out the double immunostaining with BrdU and GFP (FIG. 6B). While the expression of the transgene was observed in many dividing cells in SVZ in the case of the injection of the VSV-G and the RV-G vectors, almost no gene transfer into the dividing cells was observed in the case of the injection of the FuG-C vector. These results show that the frequency of the gene transfer into the neural stem cells and dividing cells with the FuG-C vector is very low.

Histological Procedures

For immunostaining by the avidin-biotin-peroxidase method, transverse sections (for mice: thickness of 30 μm) were prepared using a cryostat. The sections were then incubated with rabbit anti-GFP polyclonal antibody (Molecular Probes, Eugene, Oreg.: 1:2,000 dilution), and further incubated with a biotinylated goat anti-rabbit IgG antibody (Vector Laboratories, Burlingame, Calif.: 1:1,000 dilution). Immunoreaction signals were visualized by the Vectastain Elite ABC kit (Vector Laboratories, Burlingame, Calif.).

For double immunofluorescence histochemical staining, the sections were incubated with either one of the above rabbit anti-GFP polyclonal antibody or anti-choline acetyltransferase mouse antibody (Chemicon, Temecula, Calif.: 1:100 dilution). Then, the sections were incubated with FITC-conjugated goat anti-rabbit IgG and Cy3-conjugated donkey anti-mouse antibody (1:500 dilution, Jackson, ImmunoResearch Laboratories, West Groove, Pa.). Fluorescence images were captured under a confocal laser scanning microscope (LSM510, Zeiss, Thornwood, N.Y.) equipped with a filter cube having a suitable specification for FITC and Cy3 fluorescence channels. These fluorescence images were taken with an advanced CCD camera system controlled by the Zeiss Axiovision software package.

Cell Count

Immunostaining by the above avidin-biotin-peroxidase method was performed using a series of sections passing through the forebrain and the midbrain. The number of immunostained cells in each brain region was counted by a computer-controlled graphics program (NIH Image 1.62, National Institutes of Health, Bethesda, Md.). In order to identify striatum cells at the injection site of the vector, double immunofluorescence histochemical staining was performed using representative sections. In each animal, the number of immunostained cells within the target region was counted by the graphics program. Using 8 to 10 sections from each animal, a mean value per section was calculated.

Contents described in the references cited herein constitute the contents of the disclosure of the present specification as a part of the present specification.

INDUSTRIAL APPLICABILITY

The retrograde transport vector according to the present invention allows the selective gene transfer into the neurons mainly via the retrograde transport, while significantly suppressing the introduction of gene into the dividing cells such as glia cells and neural stem cells. Thus, the vector according to the present invention can reduce the risk of occurrence of cancer so as to alleviate any side effects caused by non-specific gene expression in other cells than the neurons. Therefore, the present invention provides an effective technology for gene therapy of cranial nerve diseases such as Parkinson's disease.

In addition, the present invention is to provide a novel and effective technology for experiments for gene therapy of cranial nerve diseases and for creating a disease model.

What is claimed is:

1. A chimeric envelope protein capable of pseudotyping an HIV-1 lentivirus vector system to produce pseudotyped particles comprising said chimeric envelope such that the pseudotyped virus particles can facilitate selective retrograde gene transfer into neurons, wherein the chimeric envelope protein comprises the amino acid sequence of SEQ ID NO: 2.

2. A polynucleotide encoding the chimeric envelope protein of SEQ ID NO: 2.

3. An envelope plasmid, comprising the polynucleotide of claim 2.

* * * * *

SEQUENCE LISTING

```
<160> NUMBER OF SEQ ID NOS: 6

<210> SEQ ID NO 1
<211> LENGTH: 1515
<212> TYPE: DNA
<213> ORGANISM: Artificial Sequence
<220> FEATURE:
<221> NAME/KEY: CDS
<222> LOCATION: (1)..(1515)
<223> OTHER INFORMATION: DNA Encoding Fused Polypeptide (FuG-C)

<400> SEQUENCE: 1

atg gtt ccg cag gtt ctt ttg ttt gta ctc ctt ctg ggt ttt tcg ttg       48
Met Val Pro Gln Val Leu Leu Phe Val Leu Leu Leu Gly Phe Ser Leu
1               5                   10                  15

tgt ttc ggg aag ttc ccc att tac acg ata cca gac gaa ctt ggt ccc       96
Cys Phe Gly Lys Phe Pro Ile Tyr Thr Ile Pro Asp Glu Leu Gly Pro
            20                  25                  30

tgg agc cct att gac ata cac cat ctc agc tgt cca aat aac ctg gtt      144
Trp Ser Pro Ile Asp Ile His His Leu Ser Cys Pro Asn Asn Leu Val
        35                  40                  45

gtg gag gat gaa gga tgt acc aac ctg tcc gag ttc tcc tac atg gaa      192
Val Glu Asp Glu Gly Cys Thr Asn Leu Ser Glu Phe Ser Tyr Met Glu
    50                  55                  60

ctc aaa gtg gga tac atc tca gcc atc aaa gtg aac ggg ttc act tgc      240
Leu Lys Val Gly Tyr Ile Ser Ala Ile Lys Val Asn Gly Phe Thr Cys
65                  70                  75                  80

aca ggt gtt gtg aca gag gca gag acc tac acc aac ttt gtt ggt tat      288
Thr Gly Val Val Thr Glu Ala Glu Thr Tyr Thr Asn Phe Val Gly Tyr
                85                  90                  95

gtc aca acc aca ttt aag aga aag cat ttc cgc ccc acc cca gac gca      336
Val Thr Thr Thr Phe Lys Arg Lys His Phe Arg Pro Thr Pro Asp Ala
```

-continued

```
            100                 105                 110

tgt aga gcc gcg tat aac tgg aag atg gcc ggt gac ccc aga tat gaa      384
Cys Arg Ala Ala Tyr Asn Trp Lys Met Ala Gly Asp Pro Arg Tyr Glu
        115                 120                 125

gag tcc cta cac aat cca tac ccc gac tac cac tgg ctt cga act gta      432
Glu Ser Leu His Asn Pro Tyr Pro Asp Tyr His Trp Leu Arg Thr Val
    130                 135                 140

aga acc acc aaa gag tcc ctc att atc ata tcc cca agt gtg aca gat      480
Arg Thr Thr Lys Glu Ser Leu Ile Ile Ile Ser Pro Ser Val Thr Asp
145                 150                 155                 160

ttg gac cca tat gac aaa tcc ctt cac tca agg gtc ttc cct ggc gga      528
Leu Asp Pro Tyr Asp Lys Ser Leu His Ser Arg Val Phe Pro Gly Gly
                165                 170                 175

aag tgc tca gga ata acg gtg tcc tct acc tac tgc tca act aac cat      576
Lys Cys Ser Gly Ile Thr Val Ser Ser Thr Tyr Cys Ser Thr Asn His
            180                 185                 190

gat tac acc att tgg atg ccc gag aat ccg aga cca agg aca cct tgt      624
Asp Tyr Thr Ile Trp Met Pro Glu Asn Pro Arg Pro Arg Thr Pro Cys
        195                 200                 205

gac att ttt acc aat agc aga ggg aag aga gca tcc aac ggg aac aag      672
Asp Ile Phe Thr Asn Ser Arg Gly Lys Arg Ala Ser Asn Gly Asn Lys
    210                 215                 220

act tgc ggc ttt gtg gat gaa aga ggc ctg tat aag tct cta aaa gga      720
Thr Cys Gly Phe Val Asp Glu Arg Gly Leu Tyr Lys Ser Leu Lys Gly
225                 230                 235                 240

gca tgc agg ctc aag tta tgt gga gtt ctt gga ctt aga ctt atg gat      768
Ala Cys Arg Leu Lys Leu Cys Gly Val Leu Gly Leu Arg Leu Met Asp
                245                 250                 255

gga aca tgg gtc gcg atg caa aca tca gat gag acc aaa tgg tgc cct      816
Gly Thr Trp Val Ala Met Gln Thr Ser Asp Glu Thr Lys Trp Cys Pro
            260                 265                 270

cca gat cag ttg gtg aat ttg cac gac ttt cgc tca gac gag atc gag      864
Pro Asp Gln Leu Val Asn Leu His Asp Phe Arg Ser Asp Glu Ile Glu
        275                 280                 285

cat ctc gtt gtg gag gag tta gtc aag aaa aga gag gaa tgt ctg gat      912
His Leu Val Val Glu Glu Leu Val Lys Lys Arg Glu Glu Cys Leu Asp
    290                 295                 300

gca tta gag tcc atc atg acc acc aag tca gta agt ttc aga cgt ctc      960
Ala Leu Glu Ser Ile Met Thr Thr Lys Ser Val Ser Phe Arg Arg Leu
305                 310                 315                 320

agt cac ctg aga aaa ctt gtc cca ggg ttt gga aaa gca tat acc ata     1008
Ser His Leu Arg Lys Leu Val Pro Gly Phe Gly Lys Ala Tyr Thr Ile
                325                 330                 335

ttc aac aaa acc ttg atg gag gct gat gct cac tac aag tca gtc cgg     1056
Phe Asn Lys Thr Leu Met Glu Ala Asp Ala His Tyr Lys Ser Val Arg
            340                 345                 350

acc tgg aat gag atc atc ccc tca aaa ggg tgt ttg aaa gtt gga gga     1104
Thr Trp Asn Glu Ile Ile Pro Ser Lys Gly Cys Leu Lys Val Gly Gly
        355                 360                 365

agg tgc cat cct cat gtg aac ggg gtg ttt ttc aat ggt ata ata tta     1152
Arg Cys His Pro His Val Asn Gly Val Phe Phe Asn Gly Ile Ile Leu
    370                 375                 380

ggg cct gac gac cat gtc cta atc cca gag atg caa tca tcc ctc ctc     1200
Gly Pro Asp Asp His Val Leu Ile Pro Glu Met Gln Ser Ser Leu Leu
385                 390                 395                 400

cag caa cat atg gag ttg ttg gaa tct tca gtt atc ccc ctg atg cac     1248
Gln Gln His Met Glu Leu Leu Glu Ser Ser Val Ile Pro Leu Met His
                405                 410                 415

ccc ctg gca gac cct tct aca gtt ttc aaa gaa ggt gat gag gct gag     1296
```

```
Pro Leu Ala Asp Pro Ser Thr Val Phe Lys Glu Gly Asp Glu Ala Glu
            420                 425                 430

gat ttt gtt gaa gtt cac ctc tcc aaa aat cca atc gag ctt gta gaa     1344
Asp Phe Val Glu Val His Leu Ser Lys Asn Pro Ile Glu Leu Val Glu
        435                 440                 445

ggt tgg ttc agt agt tgg aaa agc tct att gcc tct ttt ttc ttt atc     1392
Gly Trp Phe Ser Ser Trp Lys Ser Ser Ile Ala Ser Phe Phe Phe Ile
    450                 455                 460

ata ggg tta atc att gga cta ttc ttg gtt ctc cga gtt ggt atc cat     1440
Ile Gly Leu Ile Ile Gly Leu Phe Leu Val Leu Arg Val Gly Ile His
465                 470                 475                 480

ctt tgc att aaa tta aag cac acc aag aaa aga cag att tat aca gac     1488
Leu Cys Ile Lys Leu Lys His Thr Lys Lys Arg Gln Ile Tyr Thr Asp
            485                 490                 495

ata gag atg aac cga ctt gga aag taa                                 1515
Ile Glu Met Asn Arg Leu Gly Lys
            500


<210> SEQ ID NO 2
<211> LENGTH: 504
<212> TYPE: PRT
<213> ORGANISM: Artificial Sequence
<220> FEATURE:
<223> OTHER INFORMATION: Synthetic Fused Polypeptide (FuG-C)

<400> SEQUENCE: 2

Met Val Pro Gln Val Leu Leu Phe Val Leu Leu Leu Gly Phe Ser Leu
1               5                   10                  15

Cys Phe Gly Lys Phe Pro Ile Tyr Thr Ile Pro Asp Glu Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Glu Phe Ser Tyr Met Glu
    50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Arg Thr Thr Lys Glu Ser Leu Ile Ile Ile Ser Pro Ser Val Thr Asp
145                 150                 155                 160

Leu Asp Pro Tyr Asp Lys Ser Leu His Ser Arg Val Phe Pro Gly Gly
                165                 170                 175

Lys Cys Ser Gly Ile Thr Val Ser Ser Thr Tyr Cys Ser Thr Asn His
            180                 185                 190

Asp Tyr Thr Ile Trp Met Pro Glu Asn Pro Arg Pro Arg Thr Pro Cys
        195                 200                 205

Asp Ile Phe Thr Asn Ser Arg Gly Lys Arg Ala Ser Asn Gly Asn Lys
    210                 215                 220

Thr Cys Gly Phe Val Asp Glu Arg Gly Leu Tyr Lys Ser Leu Lys Gly
225                 230                 235                 240

Ala Cys Arg Leu Lys Leu Cys Gly Val Leu Gly Leu Arg Leu Met Asp
```

-continued

```
                245                 250                 255

Gly Thr Trp Val Ala Met Gln Thr Ser Asp Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Lys Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
            325                 330                 335

Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Lys Val Gly Gly
        355                 360                 365

Arg Cys His Pro His Val Asn Gly Val Phe Phe Asn Gly Ile Ile Leu
    370                 375                 380

Gly Pro Asp Asp His Val Leu Ile Pro Glu Met Gln Ser Ser Leu Leu
385                 390                 395                 400

Gln Gln His Met Glu Leu Leu Glu Ser Ser Val Ile Pro Leu Met His
                405                 410                 415

Pro Leu Ala Asp Pro Ser Thr Val Phe Lys Glu Gly Asp Glu Ala Glu
            420                 425                 430

Asp Phe Val Glu Val His Leu Ser Lys Asn Pro Ile Glu Leu Val Glu
        435                 440                 445

Gly Trp Phe Ser Ser Trp Lys Ser Ser Ile Ala Ser Phe Phe Phe Ile
    450                 455                 460

Ile Gly Leu Ile Ile Gly Leu Phe Leu Val Leu Arg Val Gly Ile His
465                 470                 475                 480

Leu Cys Ile Lys Leu Lys His Thr Lys Lys Arg Gln Ile Tyr Thr Asp
                485                 490                 495

Ile Glu Met Asn Arg Leu Gly Lys
            500


<210> SEQ ID NO 3
<211> LENGTH: 1575
<212> TYPE: DNA
<213> ORGANISM: Rabies Virus
<220> FEATURE:
<221> NAME/KEY: CDS
<222> LOCATION: (1)..(1575)
<223> OTHER INFORMATION:

<400> SEQUENCE: 3

atg gtt ccg cag gtt ctt ttg ttt gta ctc ctt ctg ggt ttt tcg ttg       48
Met Val Pro Gln Val Leu Leu Phe Val Leu Leu Leu Gly Phe Ser Leu
1               5                   10                  15

tgt ttc ggg aag ttc ccc att tac acg ata cca gac gaa ctt ggt ccc       96
Cys Phe Gly Lys Phe Pro Ile Tyr Thr Ile Pro Asp Glu Leu Gly Pro
            20                  25                  30

tgg agc cct att gac ata cac cat ctc agc tgt cca aat aac ctg gtt      144
Trp Ser Pro Ile Asp Ile His His Leu Ser Cys Pro Asn Asn Leu Val
        35                  40                  45

gtg gag gat gaa gga tgt acc aac ctg tcc gag ttc tcc tac atg gaa      192
Val Glu Asp Glu Gly Cys Thr Asn Leu Ser Glu Phe Ser Tyr Met Glu
    50                  55                  60

ctc aaa gtg gga tac atc tca gcc atc aaa gtg aac ggg ttc act tgc      240
```

-continued

```
Leu Lys Val Gly Tyr Ile Ser Ala Ile Lys Val Asn Gly Phe Thr Cys
65                  70                  75                  80

aca ggt gtt gtg aca gag gca gag acc tac acc aac ttt gtt ggt tat      288
Thr Gly Val Val Thr Glu Ala Glu Thr Tyr Thr Asn Phe Val Gly Tyr
                85                  90                  95

gtc aca acc aca ttc aag aga aag cat ttc cgc ccc acc cca gac gca      336
Val Thr Thr Thr Phe Lys Arg Lys His Phe Arg Pro Thr Pro Asp Ala
            100                 105                 110

tgt aga gcc gcg tat aac tgg aag atg gcc ggt gac ccc aga tat gaa      384
Cys Arg Ala Ala Tyr Asn Trp Lys Met Ala Gly Asp Pro Arg Tyr Glu
        115                 120                 125

gag tcc cta cac aat cca tac ccc gac tac cac tgg ctt cga act gta      432
Glu Ser Leu His Asn Pro Tyr Pro Asp Tyr His Trp Leu Arg Thr Val
    130                 135                 140

aga acc acc aaa gag tcc ctc att atc ata tcc cca agt gtg aca gat      480
Arg Thr Thr Lys Glu Ser Leu Ile Ile Ile Ser Pro Ser Val Thr Asp
145                 150                 155                 160

ttg gac cca tat gac aaa tcc ctt cac tca agg gtc ttc cct ggc gga      528
Leu Asp Pro Tyr Asp Lys Ser Leu His Ser Arg Val Phe Pro Gly Gly
                165                 170                 175

aag tgc tca gga ata acg gtg tcc tct acc tac tgc tca act aac cat      576
Lys Cys Ser Gly Ile Thr Val Ser Ser Thr Tyr Cys Ser Thr Asn His
            180                 185                 190

gat tac acc att tgg atg ccc gag aat ccg aga cca agg aca cct tgt      624
Asp Tyr Thr Ile Trp Met Pro Glu Asn Pro Arg Pro Arg Thr Pro Cys
        195                 200                 205

gac att ttt acc aat agc aga ggg aag aga gca tcc aac ggg aac aag      672
Asp Ile Phe Thr Asn Ser Arg Gly Lys Arg Ala Ser Asn Gly Asn Lys
    210                 215                 220

act tgc ggc ttt gtg gat gaa aga ggc ctg tat aag tct cta aaa gga      720
Thr Cys Gly Phe Val Asp Glu Arg Gly Leu Tyr Lys Ser Leu Lys Gly
225                 230                 235                 240

gca tgc agg ctc aag tta tgt gga gtt ctt gga ctt aga ctt atg gat      768
Ala Cys Arg Leu Lys Leu Cys Gly Val Leu Gly Leu Arg Leu Met Asp
                245                 250                 255

gga aca tgg gtc gcg atg caa aca tca gat gag acc aaa tgg tgc cct      816
Gly Thr Trp Val Ala Met Gln Thr Ser Asp Glu Thr Lys Trp Cys Pro
            260                 265                 270

cca gat cag ttg gtg aat ttg cac gac ttt cgc tca gac gag atc gag      864
Pro Asp Gln Leu Val Asn Leu His Asp Phe Arg Ser Asp Glu Ile Glu
        275                 280                 285

cat ctc gtt gtg gag gag tta gtc aag aaa aga gag gaa tgt ctg gat      912
His Leu Val Val Glu Glu Leu Val Lys Lys Arg Glu Glu Cys Leu Asp
    290                 295                 300

gca tta gag tcc atc atg acc acc aag tca gta agt ttc aga cgt ctc      960
Ala Leu Glu Ser Ile Met Thr Thr Lys Ser Val Ser Phe Arg Arg Leu
305                 310                 315                 320

agt cac ctg aga aaa ctt gtc cca ggg ttt gga aaa gca tat acc ata     1008
Ser His Leu Arg Lys Leu Val Pro Gly Phe Gly Lys Ala Tyr Thr Ile
                325                 330                 335

ttc aac aaa acc ttg atg gag gct gat gct cac tac aag tca gtc cgg     1056
Phe Asn Lys Thr Leu Met Glu Ala Asp Ala His Tyr Lys Ser Val Arg
            340                 345                 350

acc tgg aat gag atc atc ccc tca aaa ggg tgt ttg aaa gtt gga gga     1104
Thr Trp Asn Glu Ile Ile Pro Ser Lys Gly Cys Leu Lys Val Gly Gly
        355                 360                 365

agg tgc cat cct cat gtg aac ggg gtg ttt ttc aat ggt ata ata tta     1152
Arg Cys His Pro His Val Asn Gly Val Phe Phe Asn Gly Ile Ile Leu
    370                 375                 380
```

-continued

```
ggg cct gac gac cat gtc cta atc cca gag atg caa tca tcc ctc ctc      1200
Gly Pro Asp Asp His Val Leu Ile Pro Glu Met Gln Ser Ser Leu Leu
385                 390                 395                 400

cag caa cat atg gag ttg ttg gaa tct tca gtt atc ccc ctg atg cac      1248
Gln Gln His Met Glu Leu Leu Glu Ser Ser Val Ile Pro Leu Met His
                405                 410                 415

ccc ctg gca gac cct tct aca gtt ttc aaa gaa ggt gat gag gct gag      1296
Pro Leu Ala Asp Pro Ser Thr Val Phe Lys Glu Gly Asp Glu Ala Glu
            420                 425                 430

gat ttt gtt gaa gtt cac ctc ccc gat gtg tac aaa cag atc tca ggg      1344
Asp Phe Val Glu Val His Leu Pro Asp Val Tyr Lys Gln Ile Ser Gly
        435                 440                 445

gtt gac ctg ggt ctc ccg aac tgg gga aag tat gta ttg atg act gca      1392
Val Asp Leu Gly Leu Pro Asn Trp Gly Lys Tyr Val Leu Met Thr Ala
    450                 455                 460

ggg gcc atg att ggc ctg gtg ttg ata ttt tcc cta atg aca tgg tgc      1440
Gly Ala Met Ile Gly Leu Val Leu Ile Phe Ser Leu Met Thr Trp Cys
465                 470                 475                 480

aga aga gcc aat cga cca gaa tcg aaa caa cgc agt ttt gga ggg aca      1488
Arg Arg Ala Asn Arg Pro Glu Ser Lys Gln Arg Ser Phe Gly Gly Thr
                485                 490                 495

ggg ggg aat gtg tca gtc act tcc caa agc gga aaa gtc ata cct tca      1536
Gly Gly Asn Val Ser Val Thr Ser Gln Ser Gly Lys Val Ile Pro Ser
            500                 505                 510

tgg gaa tca tat aag agt gga ggt gag acc agg ctg tga                  1575
Trp Glu Ser Tyr Lys Ser Gly Gly Glu Thr Arg Leu
        515                 520


<210> SEQ ID NO 4
<211> LENGTH: 524
<212> TYPE: PRT
<213> ORGANISM: Rabies Virus

<400> SEQUENCE: 4

Met Val Pro Gln Val Leu Leu Phe Val Leu Leu Leu Gly Phe Ser Leu
1               5                   10                  15

Cys Phe Gly Lys Phe Pro Ile Tyr Thr Ile Pro Asp Glu Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Glu Phe Ser Tyr Met Glu
    50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Arg Thr Thr Lys Glu Ser Leu Ile Ile Ile Ser Pro Ser Val Thr Asp
145                 150                 155                 160

Leu Asp Pro Tyr Asp Lys Ser Leu His Ser Arg Val Phe Pro Gly Gly
                165                 170                 175

Lys Cys Ser Gly Ile Thr Val Ser Ser Thr Tyr Cys Ser Thr Asn His
            180                 185                 190
```

```
Asp Tyr Thr Ile Trp Met Pro Glu Asn Pro Arg Pro Arg Thr Pro Cys
        195                 200                 205

Asp Ile Phe Thr Asn Ser Arg Gly Lys Arg Ala Ser Asn Gly Asn Lys
    210                 215                 220

Thr Cys Gly Phe Val Asp Glu Arg Gly Leu Tyr Lys Ser Leu Lys Gly
225                 230                 235                 240

Ala Cys Arg Leu Lys Leu Cys Gly Val Leu Gly Leu Arg Leu Met Asp
                245                 250                 255

Gly Thr Trp Val Ala Met Gln Thr Ser Asp Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Lys Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Ile Pro Ser Lys Gly Cys Leu Lys Val Gly Gly
        355                 360                 365

Arg Cys His Pro His Val Asn Gly Val Phe Phe Asn Gly Ile Ile Leu
    370                 375                 380

Gly Pro Asp Asp His Val Leu Ile Pro Glu Met Gln Ser Ser Leu Leu
385                 390                 395                 400

Gln Gln His Met Glu Leu Leu Glu Ser Ser Val Ile Pro Leu Met His
                405                 410                 415

Pro Leu Ala Asp Pro Ser Thr Val Phe Lys Glu Gly Asp Glu Ala Glu
            420                 425                 430

Asp Phe Val Glu Val His Leu Pro Asp Val Tyr Lys Gln Ile Ser Gly
        435                 440                 445

Val Asp Leu Gly Leu Pro Asn Trp Gly Lys Tyr Val Leu Met Thr Ala
    450                 455                 460

Gly Ala Met Ile Gly Leu Val Leu Ile Phe Ser Leu Met Thr Trp Cys
465                 470                 475                 480

Arg Arg Ala Asn Arg Pro Glu Ser Lys Gln Arg Ser Phe Gly Gly Thr
                485                 490                 495

Gly Gly Asn Val Ser Val Thr Ser Gln Ser Gly Lys Val Ile Pro Ser
            500                 505                 510

Trp Glu Ser Tyr Lys Ser Gly Gly Glu Thr Arg Leu
        515                 520
```

<210> SEQ ID NO 5
<211> LENGTH: 6399
<212> TYPE: DNA
<213> ORGANISM: Artificial Sequence
<220> FEATURE:
<223> OTHER INFORMATION: pCAG-FuG-C

<400> SEQUENCE: 5

```
gtcgacattg attattgact agttattaat agtaatcaat tacggggtca ttagttcata      60

gcccatatat ggagttccgc gttacataac ttacggtaaa tggcccgcct ggctgaccgc     120

ccaacgaccc ccgcccattg acgtcaataa tgacgtatgt tcccatagta acgccaatag     180
```

```
ggactttcca ttgacgtcaa tgggtggact atttacggta aactgcccac ttggcagtac    240
atcaagtgta tcatatgcca agtacgcccc ctattgacgt caatgacggt aaatggcccg    300
cctggcatta tgcccagtac atgaccttat gggactttcc tacttggcag tacatctacg    360
tattagtcat cgctattacc atgggtcgag gtgagcccca cgttctgctt cactctcccc    420
atctcccccc cctccccacc cccaattttg tatttattta tttttaatt attttgtgca    480
gcgatggggg cggggggggg gggggcgcgc gccaggcggg gcggggcggg gcgaggggcg    540
gggcggggcg aggcggagag gtgcggcggc agccaatcag agcggcgcgc tccgaaagtt    600
tccttttatg gcgaggcggc ggcggcggcg gccctataaa aagcgaagcg cgcggcgggc    660
gggagtcgct gcgttgcctt cgccccgtgc cccgctccgc gccgcctcgc gccgcccgcc    720
ccggctctga ctgaccgcgt tactcccaca ggtgagcggg cgggacggcc cttctcctcc    780
gggctgtaat tagcgcttgg tttaatgacg gctcgtttct tttctgtggc tgcgtgaaag    840
ccttaaaggg ctccgggagg gccctttgtg cggggggggag cggctcgggg ggtgcgtgcg    900
tgtgtgtgtg cgtggggagc gccgcgtgcg gcccgcgctg cccggcggct gtgagcgctg    960
cgggcgcggc gcggggcttt gtgcgctccg cgtgtgcgcg aggggagcgc ggccgggggc   1020
ggtgccccgc ggtgcggggg ggctgcgagg ggaacaaagg ctgcgtgcgg ggtgtgtgcg   1080
tgggggggtg agcagggggt gtgggcgcgg cggtcgggct gtaacccccc cctgcacccc   1140
cctccccgag ttgctgagca cggcccggct tcgggtgcgg ggctccgtgc ggggcgtggc   1200
gcggggctcg ccgtgccggg cggggggtgg cggcaggtgg gggtgccggg cggggcgggg   1260
ccgcctcggg ccggggaggg ctcgggggag ggcgcggcg gccccggagc gccggcggct   1320
gtcgaggcgc ggcgagccgc agccattgcc ttttatggta atcgtgcgag agggcgcagg   1380
gacttccttt gtcccaaatc tggcggagcc gaaatctggg aggcgccgcc gcaccccctc   1440
tagcgggcgc gggcgaagcg gtgcggcgcc ggcaggaagg aaatgggcgg ggagggcctt   1500
cgtgcgtcgc cgcgccgccg tccccttctc catctccagc ctcggggctg ccgcaggggg   1560
acggctgcct tcggggggga cggggcaggg cggggttcgg cttctggcgt gtgaccggcg   1620
gctctagagc ctctgctaac catgttcatg ccttcttctt tttcctacag ctcctgggca   1680
acgtgctggt tattgtgctg tctcatcatt ttggcaaaga attcgccctt aggaaagatg   1740
gttccgcagg ttcttttgtt tgtactcctt ctgggttttt cgttgtgttt cgggaagttc   1800
cccatttaca cgataccaga cgaacttggt ccctggagcc ctattgacat acaccatctc   1860
agctgtccaa ataacctggt tgtggaggat gaaggatgta ccaacctgtc cgagttctcc   1920
tacatggaac tcaaagtggg atacatctca gccatcaaag tgaacgggtt cacttgcaca   1980
ggtgttgtga cagaggcaga gacctacacc aactttgttg gttatgtcac aaccacattt   2040
aagagaaagc atttccgccc caccccagac gcatgtagag ccgcgtataa ctggaagatg   2100
gccggtgacc ccagatatga agagtcccta cacaatccat accccgacta ccactggctt   2160
cgaactgtaa gaaccaccaa agagtccctc attatcatat ccccaagtgt gacagatttg   2220
gacccatatg acaaatccct tcactcaagg gtcttccctg gcggaaagtg ctcaggaata   2280
acggtgtcct ctacctactg ctcaactaac catgattaca ccatttggat gcccgagaat   2340
ccgagaccaa ggacaccttg tgacattttt accaatagca gagggaagag agcatccaac   2400
gggaacaaga cttgcggctt tgtggatgaa agaggcctgt ataagtctct aaaaggagca   2460
tgcaggctca agttatgtgg agttcttgga cttagactta tggatggaac atgggtcgcg   2520
```

-continued

```
atgcaaacat cagatgagac caaatggtgc cctccagatc agttggtgaa tttgcacgac   2580
tttcgctcag acgagatcga gcatctcgtt gtggaggagt tagtcaagaa aagagaggaa   2640
tgtctggatg cattagagtc catcatgacc accaagtcag taagtttcag acgtctcagt   2700
cacctgagaa aacttgtccc agggtttgga aaagcatata ccatattcaa caaaaccttg   2760
atggaggctg atgctcacta caagtcagtc cggacctgga atgagatcat cccctcaaaa   2820
gggtgtttga aagttggagg aaggtgccat cctcatgtga acggggtgtt tttcaatggt   2880
ataatattag ggcctgacga ccatgtccta atcccagaga tgcaatcatc cctcctccag   2940
caacatatgg agttgttgga atcttcagtt atccccctga tgcaccccct ggcagaccct   3000
tctacagttt tcaaagaagg tgatgaggct gaggattttg ttgaagttca cctctccaaa   3060
aatccaatcg agcttgtaga aggttggttc agtagttgga aaagctctat tgcctctttt   3120
ttctttatca tagggttaat cattggacta ttcttggttc tccgagttgg tatccatctt   3180
tgcattaaat taaagcacac caagaaaaga cagatttata cagacataga gatgaaccga   3240
cttggaaagt aactcaaatc ctgcacaaca gattcttcat gtttggacca aatcaacttg   3300
tgataccatg ctcaaagagg cctcaattat atttgagttt ttaattttta tgaaaaaaaa   3360
aaaaaaaaac ggaattcctg cagcccccaa caaccggtac ctctagaact atagctagca   3420
gatctttttc cctctgccaa aaattatggg gacatcatga agccccttga gcatctgact   3480
tctggctaat aaaggaaatt tattttcatt gcaatagtgt gttggaattt tttgtgtctc   3540
tcactcggaa ggacatatgg gagggcaaat catttaaaac atcagaatga gtatttggtt   3600
tagagtttgg caacatatgc catatgctgg ctgccatgaa caaaggtggc tataaagagg   3660
tcatcagtat atgaaacagc cccctgctgt ccattcctta ttccatagaa aagccttgac   3720
ttgaggttag attttttta tattttgttt tgtgttattt ttttctttaa catccctaaa   3780
attttcctta catgttttac tagccagatt tttcctcctc tcctgactac tcccagtcat   3840
agctgtccct cttctcttat gaagatccct cgacctgcag cccaagcttg gcgtaatcat   3900
ggtcatagct gtttcctgtg tgaaattgtt atccgctcac aattccacac aacatacgag   3960
ccggaagcat aaagtgtaaa gcctggggtg cctaatgagt gagctaactc acattaattg   4020
cgttgcgctc actgcccgct ttccagtcgg gaaacctgtc gtgccagcgg atccgcatct   4080
caattagtca gcaaccatag tcccgcccct aactccgccc atcccgcccc taactccgcc   4140
cagttccgcc cattctccgc cccatggctg actaattttt tttatttatg cagaggccga   4200
ggccgcctcg gcctctgagc tattccagaa gtagtgagga ggcttttttg gaggcctagg   4260
cttttgcaaa aagctaactt gtttattgca gcttataatg gttacaaata aagcaatagc   4320
atcacaaatt tcacaaataa agcatttttt tcactgcatt ctagttgtgg tttgtccaaa   4380
ctcatcaatg tatcttatca tgtctggatc cgctgcatta atgaatcggc caacgcgcgg   4440
ggagaggcgg tttgcgtatt gggcgctctt ccgcttcctc gctcactgac tcgctgcgct   4500
cggtcgttcg gctgcggcga gcggtatcag ctcactcaaa ggcggtaata cggttatcca   4560
cagaatcagg ggataacgca ggaaagaaca tgtgagcaaa aggccagcaa aaggccagga   4620
accgtaaaaa ggccgcgttg ctggcgtttt tccataggct ccgcccccct gacgagcatc   4680
acaaaaatcg acgctcaagt cagaggtggc gaaacccgac aggactataa agataccagg   4740
cgtttccccc tggaagctcc ctcgtgcgct ctcctgttcc gaccctgccg cttaccggat   4800
acctgtccgc ctttctccct tcgggaagcg tggcgctttc tcaatgctca cgctgtaggt   4860
atctcagttc ggtgtaggtc gttcgctcca agctgggctg tgtgcacgaa ccccccgttc   4920
```

-continued

```
agcccgaccg ctgcgcctta tccggtaact atcgtcttga gtccaacccg gtaagacacg   4980

acttatcgcc actggcagca gccactggta acaggattag cagagcgagg tatgtaggcg   5040

gtgctacaga gttcttgaag tggtggccta actacggcta cactagaagg acagtatttg   5100

gtatctgcgc tctgctgaag ccagttacct tcggaaaaag agttggtagc tcttgatccg   5160

gcaaacaaac caccgctggt agcggtggtt tttttgtttg caagcagcag attacgcgca   5220

gaaaaaaagg atctcaagaa gatcctttga tcttttctac ggggtctgac gctcagtgga   5280

acgaaaactc acgttaaggg attttggtca tgagattatc aaaaaggatc ttcacctaga   5340

tccttttaaa ttaaaaatga agttttaaat caatctaaag tatatatgag taaacttggt   5400

ctgacagtta ccaatgctta atcagtgagg cacctatctc agcgatctgt ctatttcgtt   5460

catccatagt tgcctgactc cccgtcgtgt agataactac gatacgggag ggcttaccat   5520

ctggccccag tgctgcaatg ataccgcgag acccacgctc accggctcca gatttatcag   5580

caataaacca gccagccgga agggccgagc gcagaagtgg tcctgcaact ttatccgcct   5640

ccatccagtc tattaattgt tgccgggaag ctagagtaag tagttcgcca gttaatagtt   5700

tgcgcaacgt tgttgccatt gctacaggca tcgtggtgtc acgctcgtcg tttggtatgg   5760

cttcattcag ctccggttcc caacgatcaa ggcgagttac atgatccccc atgttgtgca   5820

aaaaagcggt tagctccttc ggtcctccga tcgttgtcag aagtaagttg gccgcagtgt   5880

tatcactcat ggttatggca gcactgcata attctcttac tgtcatgcca tccgtaagat   5940

gcttttctgt gactggtgag tactcaacca agtcattctg agaatagtgt atgcggcgac   6000

cgagttgctc ttgcccggcg tcaatacggg ataataccgc gccacatagc agaactttaa   6060

aagtgctcat cattggaaaa cgttcttcgg ggcgaaaact ctcaaggatc ttaccgctgt   6120

tgagatccag ttcgatgtaa cccactcgtg cacccaactg atcttcagca tcttttactt   6180

tcaccagcgt ttctgggtga gcaaaaacag gaaggcaaaa tgccgcaaaa aagggaataa   6240

gggcgacacg gaaatgttga atactcatac tcttcctttt tcaatattat tgaagcattt   6300

atcagggtta ttgtctcatg agcggataca tatttgaatg tatttagaaa aataaacaaa   6360

taggggttcc gcgcacattt ccccgaaaag tgccacctg                          6399
```

```
<210> SEQ ID NO 6
<211> LENGTH: 16
<212> TYPE: PRT
<213> ORGANISM: Artificial Sequence
<220> FEATURE:
<223> OTHER INFORMATION: extracellular domain boundary region

<400> SEQUENCE: 6

Glu Asp Phe Val Glu Val His Leu Ser Lys Asn Pro Ile Glu Leu Val
1               5                   10                  15
```